(12) United States Patent
Kam et al.

(10) Patent No.: US 11,933,753 B2
(45) Date of Patent: Mar. 19, 2024

(54) CHEMICAL SENSING DEVICE

(71) Applicant: QI DIAGNOSTICS LIMITED, Hong Kong (CN)

(72) Inventors: Wan Lung Kam, Hong Kong (CN); Wai Fung Cheung, Hong Kong (CN); Baishu Liu, Hong Kong (CN); Bo Zheng, Hong Kong (CN)

( * ) Notice: Subject to any disclaimer, the term of this patent is extended or adjusted under 35 U.S.C. 154(b) by 802 days.

(21) Appl. No.: 17/052,528

(22) PCT Filed: May 3, 2019

(86) PCT No.: PCT/IB2019/053652
§ 371 (c)(1),
(2) Date: Nov. 3, 2020

(87) PCT Pub. No.: WO2019/211813
PCT Pub. Date: Nov. 7, 2019

(65) Prior Publication Data
US 2021/0239639 A1    Aug. 5, 2021

Related U.S. Application Data

(60) Provisional application No. 62/719,091, filed on Aug. 16, 2018, provisional application No. 62/666,179, filed on May 3, 2018.

(51) Int. Cl.
*G01N 27/12*    (2006.01)
*B01J 31/02*    (2006.01)
(Continued)

(52) U.S. Cl.
CPC ......... *G01N 27/128* (2013.01); *C01B 32/194* (2017.08); *C01B 32/198* (2017.08);
(Continued)

(58) Field of Classification Search
CPC .. G01N 27/128; G01N 27/308; G01N 33/497; C01B 32/194; C01B 32/198;
(Continued)

(56) References Cited

U.S. PATENT DOCUMENTS

2015/0122800 A1* 5/2015 Gallastegui .......... H05B 3/0004
549/543
2018/0059041 A1* 3/2018 Jelinek ................. G01N 27/304

OTHER PUBLICATIONS

Nguyen, et al., Effects of grafting methods for functionalization of graphene oxide by dodecylamine on the physical propertis of its polyurethane nanocomposites, Journal of Membrane Science 2017; 540: 108-119 (with Supplementary Information) (Year: 2017).*
(Continued)

*Primary Examiner* — Daniel C. McCracken
(74) *Attorney, Agent, or Firm* — LAW OFFICES OF ALBERT WAI-KIT CHAN, PLLC

(57) ABSTRACT

The present application describes a sensor apparatus based on chemically functionalized graphene as the sensing materials. The sensing materials is modified from graphene oxide with unique chemical process to form a group of graphene derivatives, e.g. butylamine, hexylamine, decylamine, dodecylamine, benzylamine etc., to detect volatile and non-volatile compounds, e.g. toluene, ethylacetate, ethanol, acetone, hexane etc. with high sensitivity. Pattern recognition algorithms and methods, e.g. PCA, are coupled with the sensors for detecting and quantifying specific chemical compounds. Methods of using the sensor apparatus in applications such as diagnosis of disease and food quality control are disclosed.

16 Claims, 24 Drawing Sheets

(51) Int. Cl.
*C01B 32/194* (2017.01)
*C01B 32/198* (2017.01)
*G01N 27/30* (2006.01)
*G01N 33/497* (2006.01)

(52) U.S. Cl.
CPC ......... *G01N 27/308* (2013.01); *G01N 33/497* (2013.01); *B01J 31/0237* (2013.01)

(58) Field of Classification Search
CPC ... C01B 32/192; C01B 32/182; C01B 32/184; C01B 32/186; C01B 32/188; C01B 32/19; C01B 32/196; C01B 2204/00; C01B 2204/02; C01B 2204/04; C01B 2204/06; C01B 2204/065; C01B 2204/20; C01B 2204/22; C01B 2204/24; C01B 2204/26; C01B 2204/28; C01B 2204/30; C01B 2204/32; C01B 32/20; C01B 32/205; C01B 32/21; C01B 32/215; C01B 32/22; C01B 32/225; C01B 32/23; B01J 31/0237
See application file for complete search history.

(56) References Cited

OTHER PUBLICATIONS

Pan, et al., Water-Soluble Poly(N-isopropylacrylamide)-Graphene Sheets Synthesized via Click Chemistry for Drug Delivery, Adv. Funct. Mater. 2011; 21: 2754-2763 (Year: 2011).*
Aug. 27, 2019 PCT International Search Report, Int'l App'l No. PCT/IB2019/053652.
Aug. 27, 2019 PCT Written Opinion, Int'l App'l No. PCT/IB2019/053652.
Nguyen et al., 2017, "Effects of grafting methods for functionalization of graphene oxide by dodecylamine on the physical properties of its polyurethane nanocomposites" Journal of Membrane Science, 540: 108-119.

* cited by examiner

CHEMICAL SENSING DEVICE

FIELD OF THE INVENTION

This invention relates to chemical sensing devices. In one embodiment, the invention is related to the making and uses of chemical sensors based on functionalized graphene for volatile and non-volatile chemical compounds detection.

BACKGROUND OF THE INVENTION

The hitherto known kinds of chemical sensing devices are mainly based on different sensing mechanism, such as the electrical properties[1, 2, 3] and the optical properties[4]. The chemiresistive sensing device was one of the most important ones with the advantages of high gas sensitivities, diverse sensing material library, and amenability to miniaturization for chip-based order analysis. The chemiresistive sensing device detected the chemical analyte based on the electrical resistance change of the sensor materials upon the exposure to a target chemical. Many chemiresistive electronic nose have been reported, which were based on a wide range of materials including metal oxide[5], conductive polymers[6], semiconductors[7] and carbon-based materials[2, 8].

Graphene possess several features which render its advantageous as sensing devices for volatile and non-volatile compounds detection. A particularly important feature is its enhanced surface area for detection, it is a 2D sheet of hexagonally arranged carbon atoms providing the greatest possible surface area per unit volume, so possesses consistent electrical properties. Most importantly, graphene has much higher theoretical specific area (2630 $m^2/g$) than that of commonly used sensing material of carbon nanotubes (1000 $m^2/g$), therefore graphene possesses high chemiresistivity which confers high sensitivity to chemical compounds. In the applications of gas sensing, graphene-based gas sensors were reported for the detection of NH3 and NO2 with high sensitivity at parts-per-billion (ppb) level[2]. Robinson et al. reported a gas sensor using reduced graphene oxide as the sensing material for the selective detection of acetone at ppb concentrations[9].

Lock-and-key approach, whereby a single chemical analyte is detected by a sensor, is the most frequently used approach for sensing devices. This limits the sensors to very specific targets and, therefore, restricts applications of such sensors. An array of cross-reactive sensors in conjunction with pattern recognition methods can be used for overcoming such limitations of the lock-and-key approach. Each of the cross-reactive sensors is responsive to a variety of chemical analyte and, together as an array, a distinct signature for an analyte would be produced. As a result, more than one target analyte can be detected by such sensors and individual components in multi-component mixtures may even be analyzed. Output from the sensor array can be analyzed with pattern recognition algorithms to obtain the identity, properties and concentration of any sample exposed to the sensor array.

Chemical sensors based on graphene and methods of functionalizing thereof for detecting volatile and non-volatile chemical compounds are disclosed in Gong et al., Chem. Mater., 2016, 28(8082-8118) and Tang et al., Nanotechnology, 2017, 28(055501). Although graphene has shown great potential in the application of electronic nose device, the high functionalizing cost and the difficulty in building a diverse sensing material library limited graphene's usage. Thus, there is a need for improved methods of making and uses of sensors comprising functionalized graphene for the detection of volatile and non-volatile chemical compounds.

Exhaled breath analysis has attracted great attention as one of the non-invasive and rapid techniques for clinic diagnostics.[10, 11, 12] The composition of human breath was complex, and exhaled breath contained traces of VOCs at low concentrations ranging from ppt to ppm.[11, 13] Exhaled VOCs were associated with the metabolic or pathologic processes in the human body, reflecting the change in body's chemistry. Early researchers have reported a fraction of specific disease-related VOCs biomarkers in human breath, and they were correlated to inflammatory, oxidative, microbial and neoplastic processes in human body.[12, 14] Disease-related VOCs covered a large organic compound family such as hydrocarbons, aromatic compounds, alcohols and aldehydes.[12, 15] Different VOCs were involved with different physiological processes in human body. For example, aldehydes were cytotoxic intermediates involving in gene regulation and cellular proliferation.[16, 17] and aromatic compounds could cause damage to protein and DNA leading to cancer disease.[15] Gas chromatography-mass spectrometry (GC-MS) offered an effective way to analyze and identify breath sample with high sensitivity and accuracy.[18, 19] However, GC-MS was time-consuming and expensive, and required laborious experiment operation and sample pretreatment, which greatly limited its usage.

An alternative method of analyzing complicated gas mixture is by using electronic nose. Inspired by human olfactory system, the concept of electronic nose was developed in 1982.[20] Electronic nose contained cross-reactive sensor elements arrays to mimic the function of olfactory receptors in the human nose, and the sensor elements produce distinct responses upon the exposure to VOCs analytes. Pattern recognition algorithms were used to analyze and transform the response data into fingerprint-like patterns for analytes identification and discrimination.[21, 22] Electronic noses showed a wide range of applications. e.g., in environmental control[23] and food analysis[24, 25, 26]. Compared with the conventional GC-MS, electronic nose was cheap, portable, easy to use and ideal for point-of-care clinical application. Many different types of sensors have been employed in electronic nose, among which chemiresistive-based sensor was one of the most popular types. People have explored a wide range of chemiresistive-based sensing materials, such as semiconductor metal oxides[7, 27, 28], conductive polymer[29, 30], carbon materials[31-34], gold nanoparticle[35] and hybrid materials[37, 38]. However, building and expanding a diverse library of sensing materials remain challenge issues in the research of electronic nose. To meet the challenge, the chemical functionalization of the sensing material to produce a diverse range of sensing elements provides an effective approach.[35, 39] On the other hand, chemical functionalization could change the electric properties of the sensing materials, rendering the sensing materials unsuitable as the sensing element. Much effort was still required to develop an effective functionalization approach for preparing versatile and sensitive sensing materials.

SUMMARY OF THE INVENTION

The present invention provides an electronic device comprising at least one functionalized graphene sensor for the detection of volatile and non-volatile chemical compounds. In one embodiment, the sensor of the present invention has high chemiresistivity to chemical compounds, and is thus more sensitive than known sensing materials serving the same purpose. In another embodiment, said at least one functionalized graphene sensor is functionalized graphene oxide sensor.

The present invention further provides a system comprising an electronic device comprising an array of chemically sensitive sensors of functionalized graphene oxide in conjunction with pattern recognition analyzer, wherein the pattern recognition analyzer uses methods such as artificial neural networks and principal component analysis to detect as well as quantify specific volatile and non-volatile chemical compounds.

The present invention also provides a method to synthesize a graphene based sensing material comprising the functionalizing carbodiimide crosslinker chemistry and the reduction of graphene oxide methods. In one embodiment, the method comprises first functionalization of graphene oxide then reduction to synthesize the sensing material with high sensing capabilities and reduced cost in production of graphene based electronic device.

DETAILED DESCRIPTION OF THE INVENTION

In one embodiment, the present invention provides an electronic device comprising at least one sensor of functionalized graphene oxide for the detection of specific volatile organic compounds (VOCs). The invention further provides a system comprising an array of sensors of functionalized graphene oxide and pattern recognition analyzer which utilizes algorithms such as principal component analysis and neural networks. Further disclosed are methods for detecting and classifying certain biomarkers for diagnostic and prognostic purposes.

Figure 1:
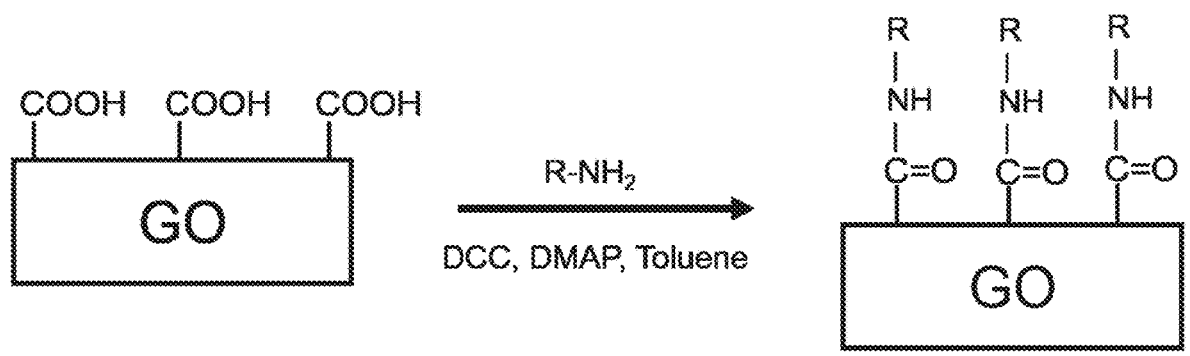
FIG. 1 shows the functionalization of the graphene oxide (GO).

Graphene oxide was easier to functionalize with target molecules due to the reactive functional groups (See FIG. 1). The carbodiimide crosslinker chemistry helped form the amide bonds between the carboxylic acids and the primary amines. The carboxyl group on the graphene oxide offered an effective way to covalently functionalize the graphene oxide. The carboxyl group of alkyl amine used comprises at least one of butylamine, hexylamine, decylamine, dodecylamine and benzylamine, to covalently functionalize the graphene oxide. The graphene oxide was also further reduced into graphene to become electrically conductive, which is essential to produce the electrical resistance signal in the gas sensing.

Figure 2:
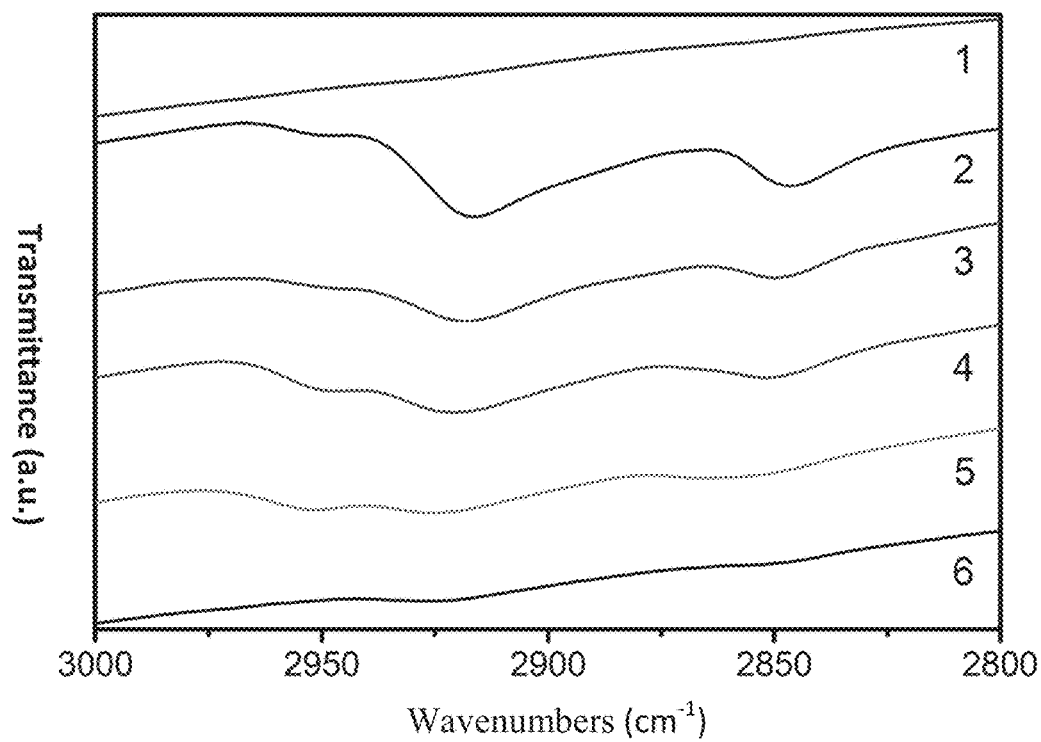
FIG. 2 shows the Fourier-transform infrared spectroscopy (FT-IR) spectra of the functionalized graphene (1.GO; 2.dodecylamine; 3.decylamine; 4.hexylamine; 5.butylamine; 6.benzylamine).

The functionalized graphene oxide sensing materials were characterized by Fourier-transform infrared spectroscopy (FT-IR). The major difference of the functionalized amine molecules were their alkyl groups. FIG. 2 showed the FT-IR spectra ranging from 3000 $cm^{-1}$ to 2800 $cm^{-1}$, and this spectrum range was the indicator of the alkyl group. Compared with the original graphene oxide, the functionalized graphene presented new absorbance brands at about 2920 $cm^{-1}$ and 2850 $cm^{-1}$, which indicated the covalently functionaliization of the graphene with the target amine molecules. Besides, as the length of alkyl carbon chain became shorter, the decrease of the absorbance brands intensity, which also matched the chemical structure of the target amine molecules.

Figure 3:
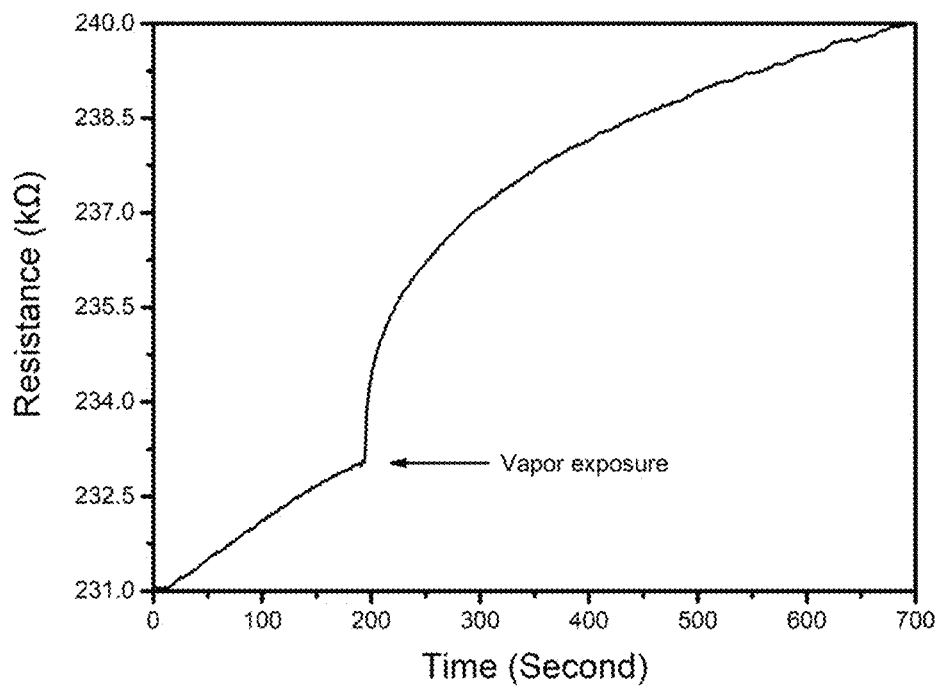
FIG. 3 shows the resistance change of decylamine functionalized graphene upon the exposure to 300 ppm ethyl acetate.

In one embodiment, the functionalized graphene was exposed to solvent vapour injected into a gas chamber (e.g. by a syringe). FIG. 3 showed the resistance response of decylamine functionalized graphene towards 300 ppm ethyl acetate vapour, which was the representative resistance response of the functionalized graphene. Upon exposure to the solvent vapour, the resistance had an initial sharp increase immediately, and then became saturated by the solvent vapour and presented a slower increase in the later stage of the vapour introduction.

Figure 4:
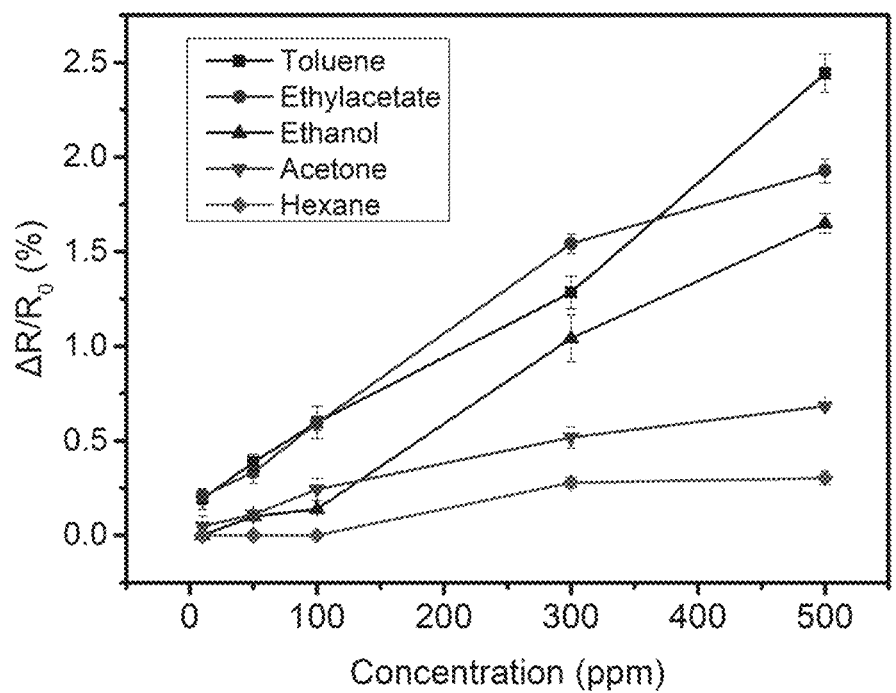
FIG. 4 shows the resistance response of decylamine functionalized graphene upon the exposure to different concentrations of the common solvent vapours.
Figure 5:
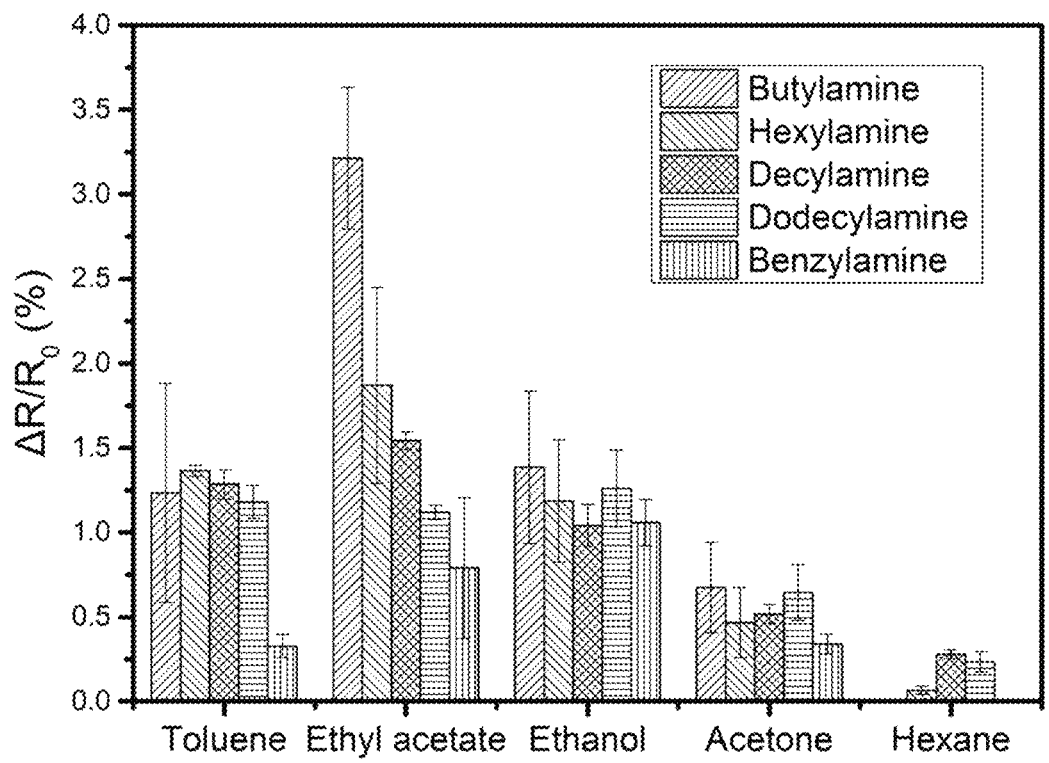
FIG. 5 shows the resistance change of different functionalized graphene upon exposure to different solvent vapour at 300 ppm concentration.

The functionalized graphene had different resistance response towards different concentrations of solvent vapour, such as the decylamine functionalized graphene in FIG. 4. Besides, as the concentration of the solvent vapour became higher, the functionalized graphene showed larger resistance response. The resistance changes of the interdigitated electrodes arrays of the electronic chemical sensor were monitored under the atmosphere of some typical VOCs species. FIG. 5 shows the resistance change of different functionalized graphene towards different solvent vapour at 300 ppm concentration. The VOCs induced a sudden resistance change of the modified graphene. Different modified graphene species have different resistance change signal towards the VOCs exposure. The response of the resistance was converted as $\Delta R/R0$, in which $\Delta R$ was the resistance change of modified graphene after VOC exposure, and R0 was the initial resistance of modified graphene before VOC exposure.

In one embodiment, the present invention provides an electronic device comprising at least one chemically sensitive sensor for the detection of chemical compounds, wherein the chemically sensitive sensor comprises at least one functionalized graphene sensing material. In one embodiment, said chemical compounds are volatile and/or non-volatile chemical compounds. In another embodiment, the electronic device enables detection of minute quantities of volatile organic compounds (VOCs). In a further embodiment, said VOCs are biomarkers for diagnostic and prognostic purposes.

In one embodiment, the present invention provides a system for detecting VOCs, comprising an array of sensors of functionalized graphene oxide, and a pattern recognition analyzer, wherein the pattern recognition analyzer receives sensor signal outputs and compares them to stored data. In another embodiment, the present invention further provides a method of using said system for detecting of VOCs from the breath of a subject. In one embodiment, the VOCs to be detected are indicative of a disease or disorder in a subject.

In one embodiment, the present invention further provides a system and method for diagnosing a disease or disorder in a subject comprising exposing an electronic device comprising an array of chemically sensitive sensors to the breath of a subject, wherein the chemically sensitive sensors comprise functionalized graphene oxide, and using pattern recognition algorithms to receive sensor output signals and compare them to stored data to identify compounds indicative of a disease or disorder.

In one embodiment, the present invention further provides a system and method for diagnosing a disease in a subject comprising exposing an electronic device comprising an array of chemically sensitive sensors to the headspace of a container in which a bodily fluid of the subject has been deposited, wherein the chemically sensitive sensors comprise functionalized graphene oxide, and using pattern recognition algorithms to receive sensor output signals and compare them to stored data to identify compounds indicative of a disease or disorder. In one embodiment, said bodily fluids comprises serum, urine, faeces, sweat, vaginal discharge, saliva or sperm In one embodiment, the disease or disorder to be diagnosed can be acute asthma, hepatic encephalopathy, rheumatoid arthritis, schizophrenia, ketosis, cardiopulmonary disease, uremia, diabetes mellitus, larynx cancer, dysgeusia/dysosmia, cystinuria, cirrhosis, histidinemia, tyrosinemia, halitosis or phenylketonuria. In another embodiment, the present invention provides a method of using the chemically sensitive sensors disclosed herein to diagnose cancer and cardiovascular disease.

In one embodiment, the present invention provides a method of using the system of the present invention to detect VOC in an edible sample, comprising the steps of: (a) collecting a sample of VOCs from said edible sample, (b) exposing an array of chemically sensitive sensors of functionalized graphene oxide to said VOCs. and (c) using pattern recognition algorithms to determine the characteristics of selected VOCs. In one embodiment, said edible can be drugs, herbs, food or drinks. In another embodiment, the characteristics of selected VOCs comprises composition or concentration. In another embodiment, the characteristics of selected VOCs is for determining quality of said edible sample. In yet another embodiment, the characteristics of selected VOCs is for determining spoilage of said edible sample.

In one embodiment, this invention provides a sensor array for detecting at least one target chemical from a sample. In one embodiment, said sensor array comprises a plurality of sensing elements, each sensing element comprises a reduced graphene oxide modified by an amine distinct from the other sensing elements; wherein each sensing element exhibit a different resistance response when exposed to said target chemical to produce a response pattern specific to said target chemical.

In one embodiment, said amine comprises one or more organic amine compounds. In another embodiment, said one or more organic amine compound comprises one or more selected from the group consisting of ethylamine, hexylamine, octylamine, benzylamine, 2-(4-chlorophenyl)ethylamine, 1-(2-aminoethyl)piperidine, 1,3-diaminopropane, amino poryphyrins and tyramine In one embodiment, said sensor array further comprises a sensing element comprising non-modified reduced graphene oxide.

In one embodiment, said sample is in gaseous form.

In one embodiment, said target chemical comprises one or more selected from the group consisting of toluene, ethyl acetate, ethanol, acetone, hexane, 2-ethylhexanol, nonanal, 3-methylhexane, 5-ethyl-3-methyloctane, iso-nonane, isoprene, styrene, undecane and ethylbenzene.

In one embodiment, said reduced graphene oxide are deposited on predetermined geometries on said sensing element.

In one embodiment, said sensing elements has a sensitivity of at least 25 ppm.

In one embodiment, said sensor array functions at room temperature. In one embodiment, this invention provides a method to analyze the response pattern from the sensor array of this invention. In one embodiment, said method comprises the steps of: (a) Obtaining a response characteristic from each of said plurality of sensing elements; (b) Analyzing said response characteristic using a pattern recognition algorithm; and (c) Comparing the results from (b) with a library of known chemicals to identify said target chemical.

In one embodiment, said pattern recognition algorithm comprises principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

In one embodiment, said amine comprises one or more selected from the group consisting of ethylamine, hexylamine, octylamine, benzylamine, 2-(4-chlorophenyl)ethylamine, 1-(2-aminoethyl)piperidine, 1,3-diaminopropane, amino poryphyrins and tyramine.

In one embodiment, said target chemical comprises one or more selected from the group consisting of toluene, ethyl acetate, ethanol, acetone, hexane, 2-ethylhexanol, nonanal, 3-methylhexane, 5-ethyl-3-methyloctane, iso-nonane isoprene, styrene, undecane and ethylbenzene.

In one embodiment, said response characteristic comprises one or more of peak response, area under curve, and relative resistance change.

In one embodiment, this invention provides a device for detecting at least one target chemical from a sample, comprising the sensor array of this invention.

In one embodiment, this invention provides a method for using the sensor array of this invention for detecting a disease in a subject, comprising the steps of: (a) Obtaining a breath sample from said subject; (b) Providing said breath sample to said sensor array; (c) Recording response characteristics from each of said plurality of sensing elements; (d) Analyzing said response characteristics using a pattern recognition algorithm; (e) Identifying said disease by comparing the results from (d) with a library of known diseases and a reference response pattern from one or more healthy subjects.

In one embodiment, said disease is selected from the group consisting of lung cancer, colorectal cancer and heart failure.

In one embodiment, said method further determines subtype of the lung cancer or heart failure.

In one embodiment, said target chemical comprises one or more selected from the group consisting of toluene, ethyl acetate, ethanol, acetone, hexane, 2-ethylhexanol, nonanal, 3-methylhexane, 5-ethyl-3-methyloctane, iso-nonane isoprene, styrene, undecane and ethylbenzene.

In one embodiment, said amine comprises one or more selected from the group consisting of ethylamine, hexylamine, octylamine, benzylamine, 2-(4-chlorophenyl)ethylamine, 1-(2-aminoethyl)piperidine, 1,3-diaminopropane, amino poryphyrins and tyramine.

In one embodiment, said pattern recognition algorithm comprises principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

In one embodiment, said response characteristic comprises one or more of peak response, area under curve, and relative resistance change.

In one embodiment, this invention provides a method to synthesize amine functionalized reduced graphene oxide, comprising the steps of: (a) Dispersing graphene oxide in an organic solvent to form a first solution; (b) Reacting said first solution with one or more amines, an activation crosslinker and a catalyst; (c) Obtaining a product from step (b) by centrifugation; (d) Dispersing said product in DMF to form a second solution; and (e) Reducing said product in said second solution to form said amine functionalized reduced graphene oxide. In one embodiment, the product in the second solution is reduced using $NH_3$ and hydrazine.

In one embodiment, said organic solvent comprises toluene or benzene.

In one embodiment, said one or more amine comprises one or more selected from the group consisting of ethylamine, hexylamine, octylamine, benzylamine, 2-(4-chlorophenyl)ethylamine, 1-(2-aminoethyl)piperidine, 1,3-diaminopropane, amino poryphyrins and tyramine.

In one embodiment, said activation crosslinker comprises dicyclohexylcarbodiimide.

In one embodiment, said catalyst comprises 4-dimethylaminopyridine.

In one embodiment, said step (b) comprises heating said first solution to 80° C. In another embodiment, said step (b) further comprises stirring for 2 days.

In one embodiment, said step (e) comprises heating said second solution to 90° C.

The principles of the present invention are demonstrated by means of the following non-limitative examples. The invention will be better understood by reference to the Experimental Details which follow, but those skilled in the art will readily appreciate that the specific experiments detailed are only illustrative, and are not meant to limit the invention as described herein, which is defined by the claims which follow thereafter. Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

Preparation of the Functionalized Graphene

First, graphene oxide (GO) were prepared by the oxidation of graphite powder using the modified Hummers' methods.[40] After the preparation of the GO, 100 mg GO was dispersed in 50 mL toluene, and 3.75 mmol target amine species (butylamine, hexylamine, decylamine, dodecylamine and benzylamine) was added in the solution with 3.75 mmol dicyclohexylcarbodiimide (DCC) as the activation crosslinker. The 4-dimethyl-aminopyridine (DMAP) was used as the catalysis, and the reaction was carried out at 90° C. for 2 days. The product was obtained by centrifugation, and then was dispersed in DMF to form 0.25 mg/mL solution using ultrasound. Finally, 375 μL NH3 was added into 100 mL the solution, and 50 μL hydrazine was added to reduce the functionalized graphene oxide at 95° C. for 2 hours.

Example 2

Fabrication of the Gas Sensor

Figure 6:
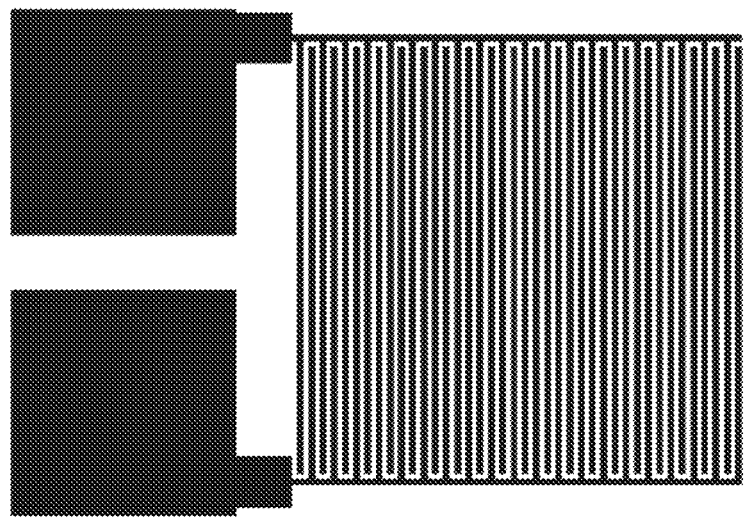
FIG. 6 shows the design of the interdigitated electrode.
Figure 7:
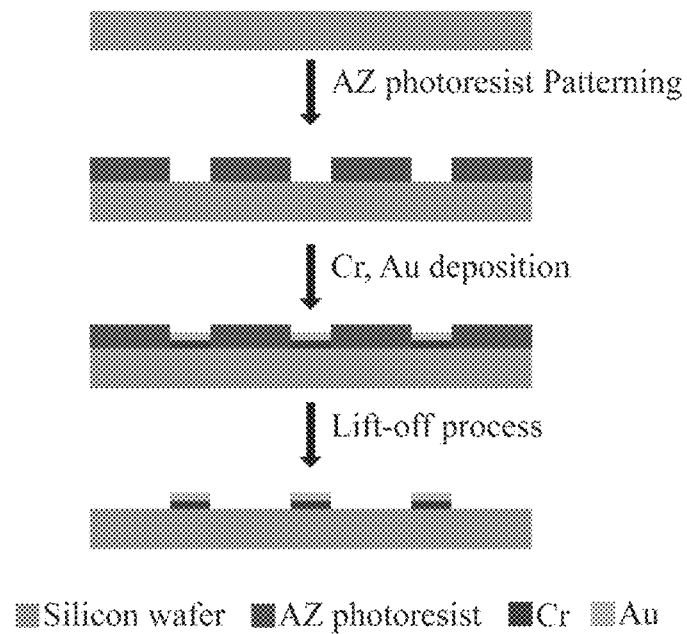
FIG. 7 shows a schematic diagram of the fabrication of the interdigitated electrodes.
Figure 8:
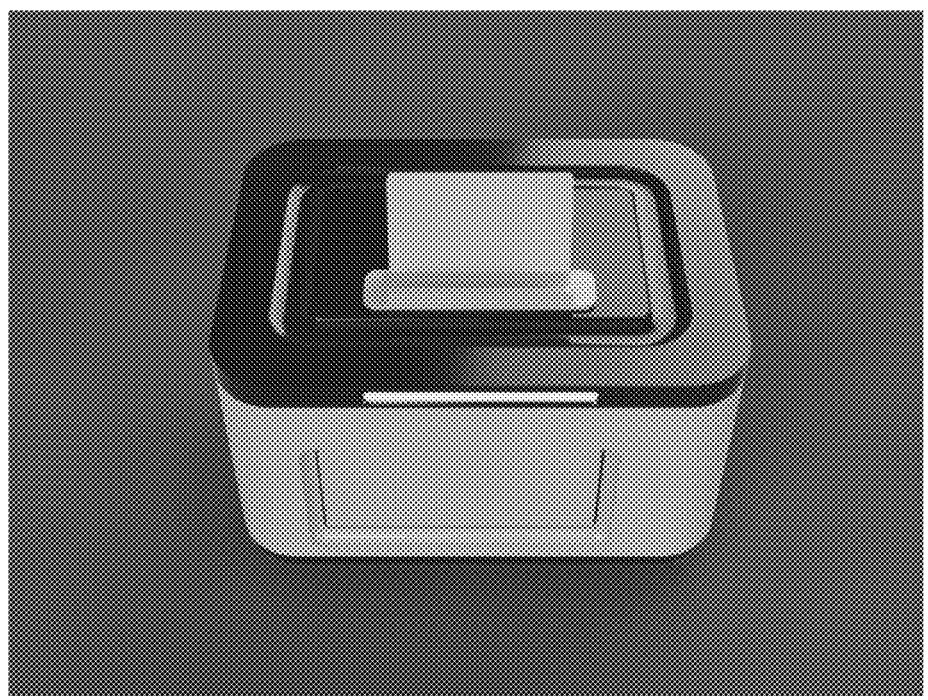
FIG. 8 shows a prototype diagram of the chemical sensing device (front).
Figure 9:
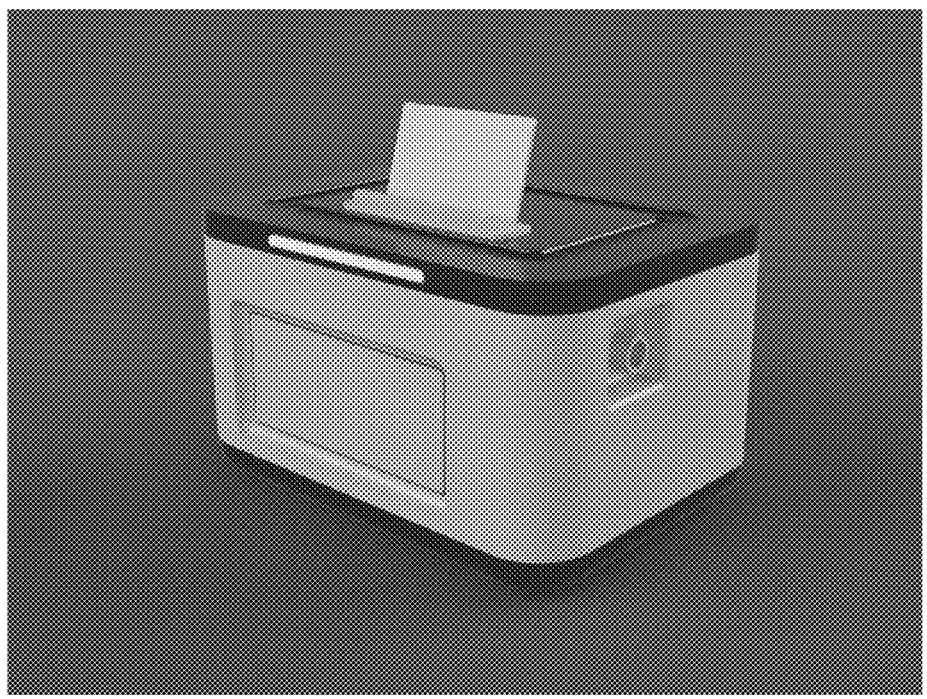
FIG. 9 shows a prototype diagram of the chemical sensing device (side). Samples can be loaded via an inlet on the side, for example, by a syringe or breath collection apparatus.

The interdigitated electrode was prepared by photolithography. The schematic diagram of the design and the fabrication process of the interdigitated electrode were shown in FIGS. 6 and 7. The width of the interdigitated electrode is 50 μm, and the gap between adjacent electrode is also 50 μm. Protective AZ photoresist pattern was first formed on the SiO2 wafer by photolithography. Cr film of 5 nm thickness was deposited on the substrate followed by another deposition of 100 nm-thick Au film on top. Finally, the AZ photoresist was removed, resulting in the interdigitated electrodes.

0.5 mg/mL functionalized graphene ink was dispersed in DMF, and 10 μL ink was deposited on the interdigitated electrode. The ink was dried on the interdigitated electrode under nitrogen flow.

Example 3

Test of the VOCs

The gas sensor was placed in the gas chamber, and the resistance of the gas sensor was monitored by the multimeter (Keithley, 2000) continuously over time. Before the gas injecting, the air in the gas chamber was removed by a vacuum pump for at least 5 minutes, and then the chamber was open to the atmosphere. The vapor with pre-determined volume was injected into the gas chamber using the gas-tight syringe to generate the desired concentration.

Example 4

In one embodiment, this invention further provides a procedure for building a library of functionalized reduced graphene oxide (rGO) and a graphene-based electronic nose for exhaled breath biomarkers identification and discrimination at room temperature. The functionalized rGO was prepared by reducing and modifying graphene oxide (GO) with chemically diverse amine ligands. Eight different functionalized rGO plus the rGO were then used to build the chemiresistive senor arrays in the electronic nose. Four cancer-related breath biomarkers, ethanol, 2-ethylhexanol, nonanal and ethylbenzene, were used as the model volatile organic compounds (VOCs) analytes. The electronic nose showed linear electric resistance responses to the biomarkers concentrations in the range of 25 to 125 ppm and the responses were stable during 10 cycles VOC exposures. Principal component analysis (PCA) pattern demonstrated the electronic nose could successfully identify and discriminate the four model VOCs analytes and binary VOC mixtures. The procedure of building the rGO library was simple and yielded consistent performance. More versatile and sensitive electronic noses will be constructed based on the functionalized rGO library with potential applications in recognition and quantitative measurement of VOCs for health monitoring and disease diagnosis.

In one embodiment, a procedure of building a library of functionalized rGO was developed and a graphene-based electronic nose was constructed to validate the procedure. The electronic nose consisted of nine gas sensors, which were made of rGO and eight different functionalized rGO. To prepare the functionalized rGO, GO was reduced and covalently modified with different amine ligands via nucleophilic substitution and carbodiimide crosslinking. Four VOCs, ethanol, 2-ethylhexanol, nonanal and ethylbenzene, were chosen as the model analytes, which have been proven to be the VOCs biomarkers in human breath.[15, 41-43] The electronic nose was tested against the VOCs analytes on the cross-reactive sensing ability and stable sensing responses.

Figure 11A:
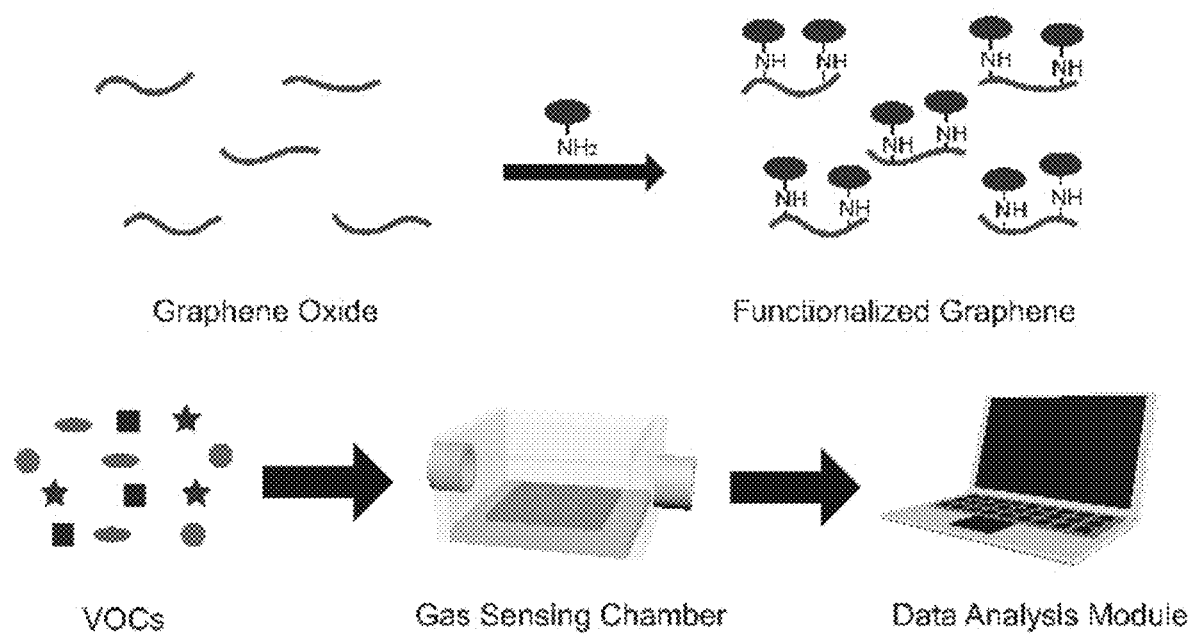
FIG. 11A shows the schematic description for the preparation of functionalized graphene with amine molecules and the experiment setup of the electronic nose for gas sensing.
Figure 11B:
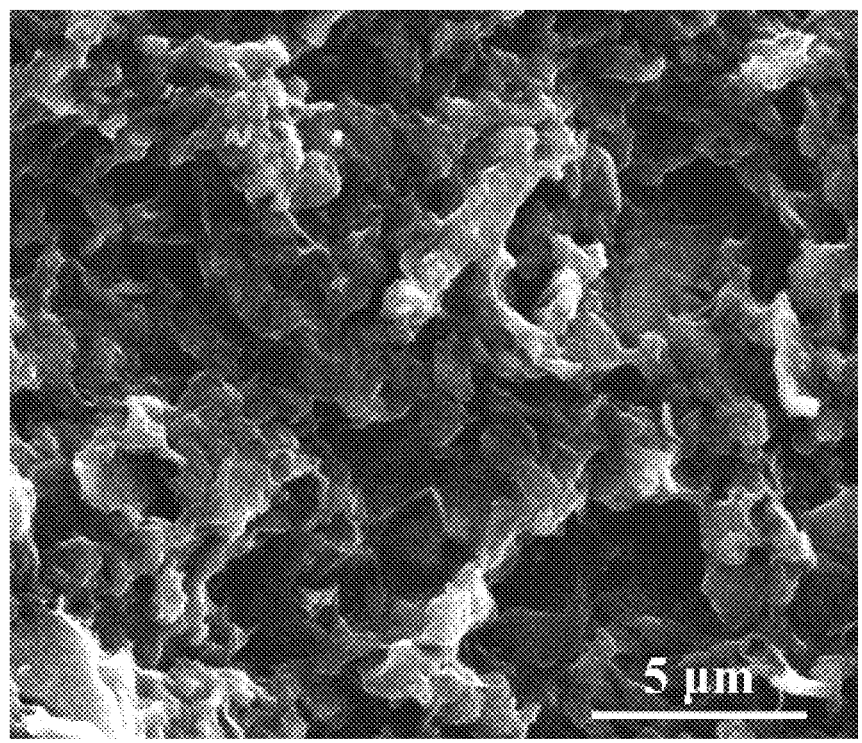
FIG. 11B shows the SEM image of the octylamine-rGO.

The functionalization of the sensing materials was an important part in electronic nose development, which greatly affected the performance of the electronic nose. The diversity of the sensing materials could enhance the cross-reactive sensing ability of the electronic nose. A facile chemical functionalization method was used to prepare a library of different functionalized rGO, and the overall scheme for preparation and sensing workflow of the electronic nose was shown in FIG. 1A. Graphene oxide was chosen as the sensing material precursor based on the following reasons. First, oxygen-containing functional groups on GO surface such as —OH, —COOH, and —C—O—C— offered many reactive sites for chemical functionalization to achieve physical and chemical properties tuning. Second, the highly conductive graphene based structure provided measurable resistance even after the conjugation of various ligands. Third, the high surface area of graphene facilitated the interactions between the sensing materials and the VOCs and brought with high sensitivity. To prepare a library of functionalized rGO. GO was reduced and covalently modified with amine-containing molecules in one-step synthesis. Amine-containing molecules could be conjugated to graphene via two ways. One was the nucleophilic substitution between the amine groups of target molecules and the epoxide groups of GO, and the other was carbodiimide catalyzed amide formation between the amine groups of target molecules and the carboxylic groups of GO.[44-47] Eight amine-containing molecules with different chemical structures were chosen to change the interactions between sensing materials and the VOCs biomarkers for cross-reactive sensing ability enhancement. Table 1 summarized the chemical structures of the functionalized amines ligands family. In the electronic nose of this invention, rGO and eight different amine-functionalized rGO were used as sensing elements. The diversity of amine ligands provided the electronic nose with cross-reactive sensing units so that the electronic nose could produce simultaneous multiple analytes information for analytes identification and discrimination. The structure properties of the functionalized rGO was studied, and octylamine-functionalized rGO (octylamine-rGO) was chosen as the model functionalized rGO to demonstrate the functionalization result. The Scanning Electron Microscopy (SEM) images showed that octylamine-rGO appeared rough with wrinkled surface morphology (FIG. 11B).

TABLE 1

Chemical Structures Of The Functionalized Amines Ligands Family

| Name | Chemical structure |
|---|---|
| ethylamine | CH$_3$CH$_2$NH$_2$ |
| hexylamine | CH$_3$(CH$_2$)$_5$NH$_2$ |
| octylamine | CH$_3$(CH$_2$)$_7$NH$_2$ |
| benzylamine | C$_6$H$_5$CH$_2$NH$_2$ |
| 2-(4-chlorophenyl)ethylamine | Cl-C$_6$H$_4$-CH$_2$CH$_2$NH$_2$ |
| 1-(2-aminoethyl)piperidine | piperidine-CH$_2$CH$_2$NH$_2$ |
| 1,3-diaminopropane | H$_2$N-(CH$_2$)$_3$-NH$_2$ |
| tyramine | HO-C$_6$H$_4$-CH$_2$CH$_2$NH$_2$ |

Figure 12A:
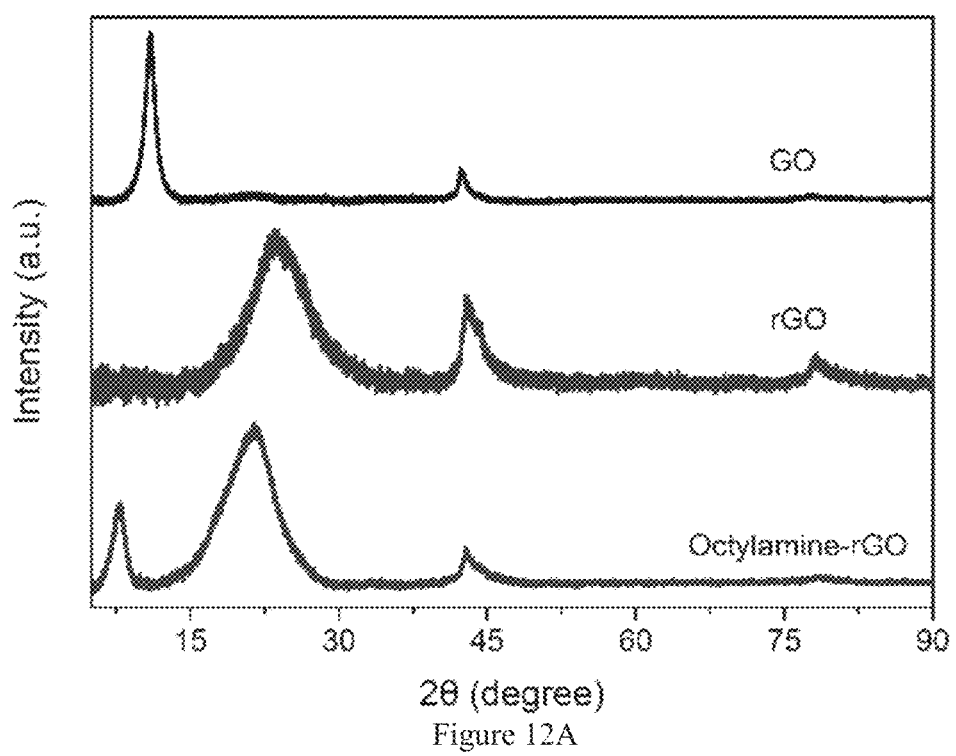
FIG. 12A shows the XRD spectra of GO, rGO and octylamine-rGO.

The X-ray diffraction (XRD) patterns of GO, rGO and octylamine-rGO were shown in FIG. 12A. The diffraction peak at 11° in GO corresponded to an interlayer distance of 0.80 nm. After chemical reduction with hydrazine, the diffraction in rGO showed a broad peak at 23.70° with a smaller interlayer distance of 0.37 nm. The decrement in interlayer spacing could be attributed to the removal of the oxygen-containing functional groups and restacking of rGO. However, the diffraction peak of octylamine-rGO shifted to 7.8° after the rGO was functionalized with amine ligands, showing the larger interlayer distance of 1.13 nm. The increase of the interlayer distance of octylamine rGO indicated the intercalation of the octyl chain.

Figure 12B:
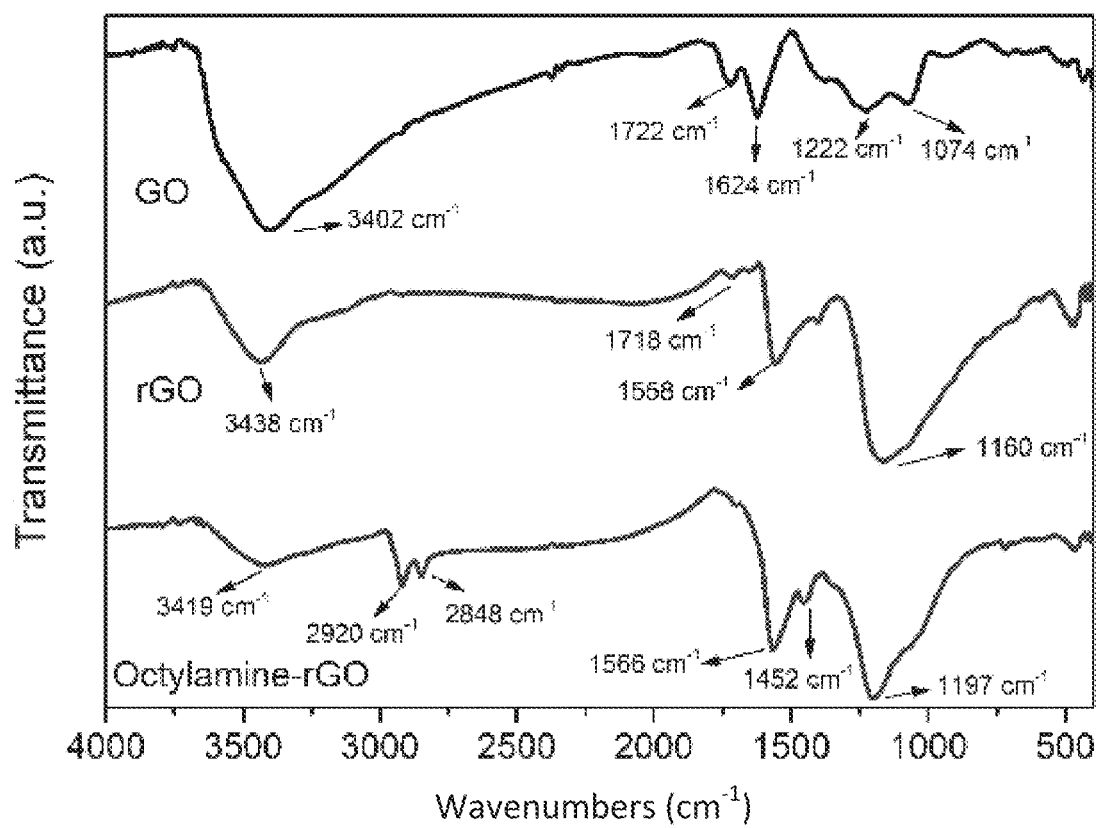
FIG. 12B shows the FT-IR spectra of GO, rGO and octylamine-rGO.

The Fourier transform infrared spectroscopy (FT-IR) was used to characterize the chemical structures of GO, rGO and octylamine-rGO (FIG. 12B). In the FT-IR spectrum of GO, the broad and intensive band at 3402 cm$^{-1}$ could be assigned to the hydroxyl groups. The characteristic bands of GO also appeared at 1722 cm$^{-1}$ (C=O stretching), 1624 cm$^{-1}$ (C=C in aromatic ring), 1222 cm$^{-1}$ (C—OH stretching) and 1074 cm$^{-1}$ (C—O—C in epoxide). Compared with GO, the hydroxyl group at 3438 cm$^{-1}$ and the carbonyl group at 1718 cm$^{-1}$ largely decreased in the spectrum of rGO due to the chemical reduction. The characteristic bands at 1558 cm$^{-1}$ and 1160 cm$^{-1}$ could be attributed to C=C skeletal vibration and C—O stretching vibration. As for the spectrum of octylamine-rGO, two new bands at 2920 cm$^{-1}$ and 2848 cm$^{-1}$ should be attributed to the C—H stretching, and the band at 1452 cm$^{-1}$ could be assigned to the C—H bending. The new bands in combination indicated the existence of the octyl chain on the functionalized rGO. The strong band at 1197 cm$^{-1}$ corresponded to the C—N stretching, implying the formation of covalent bond between rGO and the amine ligands.

Figure 12C:
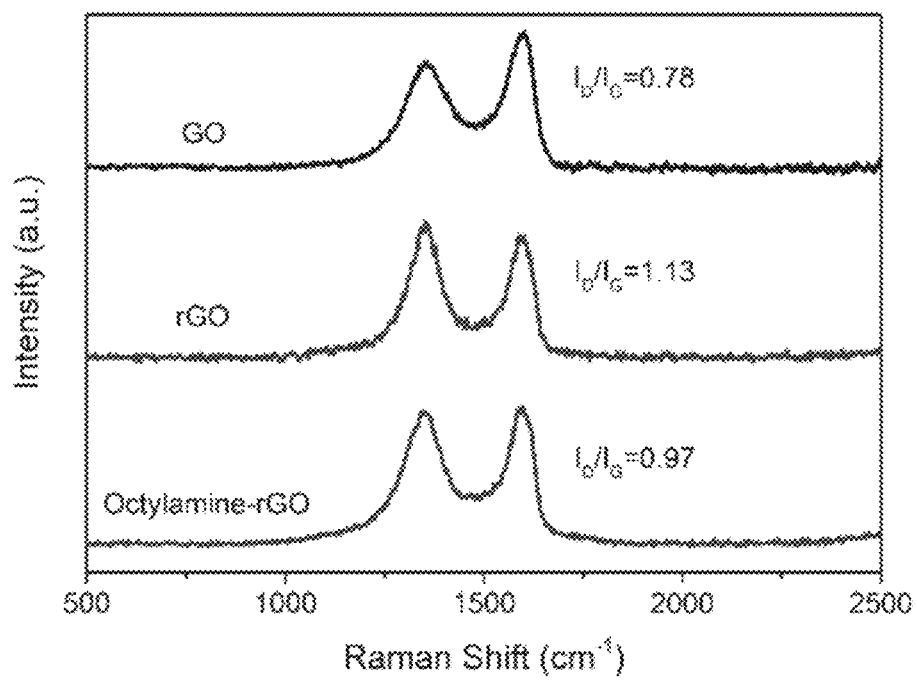
FIG. 12C shows the Raman spectra of GO, rGO and octylamine-rGO.

The structure properties of the functionalized rGO were also investigated with Raman spectroscopy. The Raman spectra of the GO, rGO and octylamine-rGO were shown in FIG. 12C. In the Raman spectrum of GO, we observed the typical D band at 1353 cm$^{-1}$ and the G band at 1602 cm$^{-1}$ with D/G intensity ratio of 0.78. The G band in rGO and octylamine-rGO shifted to low frequency at 1591 cm$^{-1}$ and 1593 cm$^{-1}$ respectively, indicating the restoration of the graphitic sp$^2$-carbon network.[46, 47] The D/G intensity ratio was found to be 1.13 in the rGO and 0.97 in octylamine-rGO, both of which were higher than that in GO. The increase of the D/G intensity indicated a decrease in of the average size of the sp$^2$ domains after the reduction of GO.

Figure 12D:
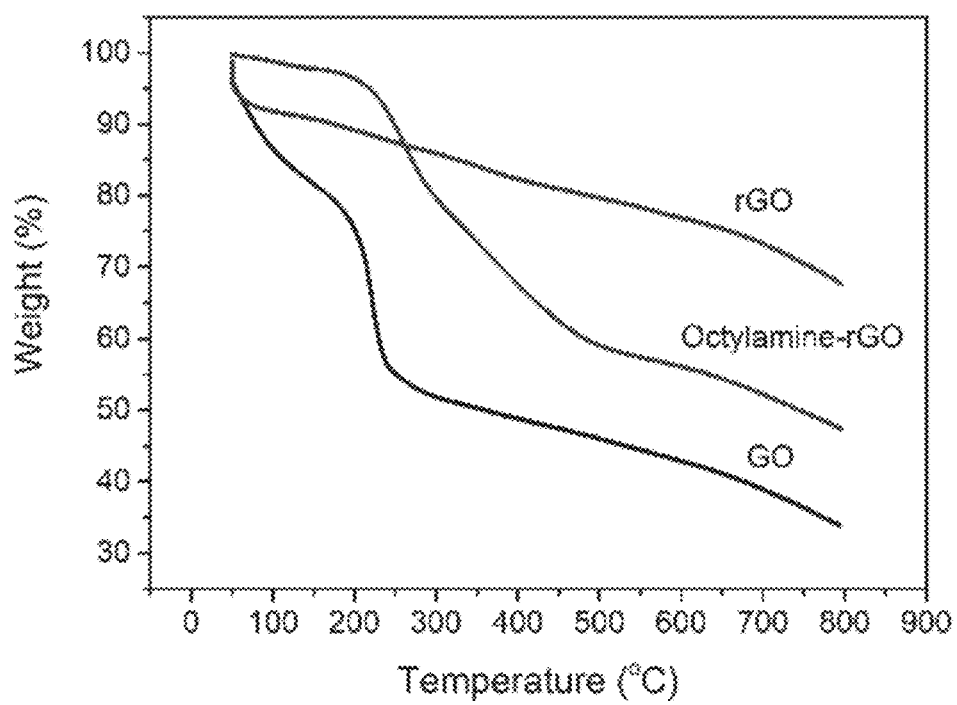
FIG. 12D shows the TGA curves of GO, rGO and octylamine-rGO.

The thermal stability of GO, rGO and octylamine-rGO was characterized by thermogravimetric analysis (TGA) under nitrogen atmosphere (FIG. 12D). GO was thermally unstable, and exhibited a significant mass loss of about 20% between 190° C. and 250° C. due to the decomposition of the oxygen-containing functional groups on the GO surface, rGO appeared more stable, and no large mass loss was observed because of the removal of the oxygen-containing functional groups after chemical reduction. However, the functionalization of octylamine allowed octylamine-rGO present different thermal behavior in TGA. Compared with the rapid weight loss below 150° C. in GO and rGO due to the removal of adsorbed water, the octyl chain on the surface of the octylamine-rGO enhanced the hydrophobicity and reduced the water adsorption so that octylamine-rGO had negligible weight loss below 150° C. Octylamine-rGO exhibited a mass loss of about 35% between 200° C. and 500° C., which could be attributed to the decomposition of covalently bonded octylamine.[48]

Figure 13A:
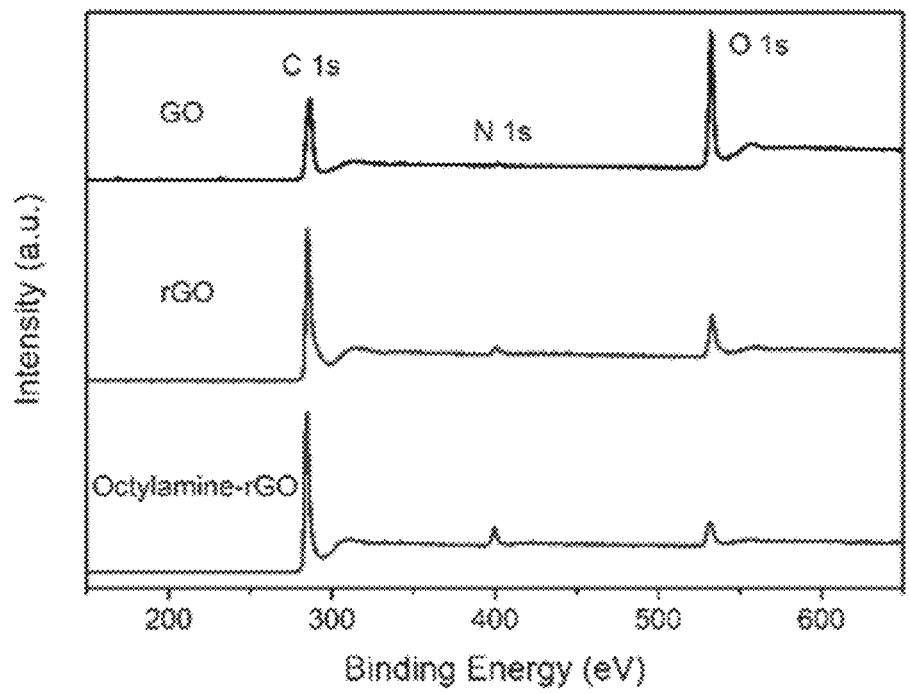
FIG. 13A shows XPS survey spectra of GO, rGO and octylamine-rGO.
Figure 13B:
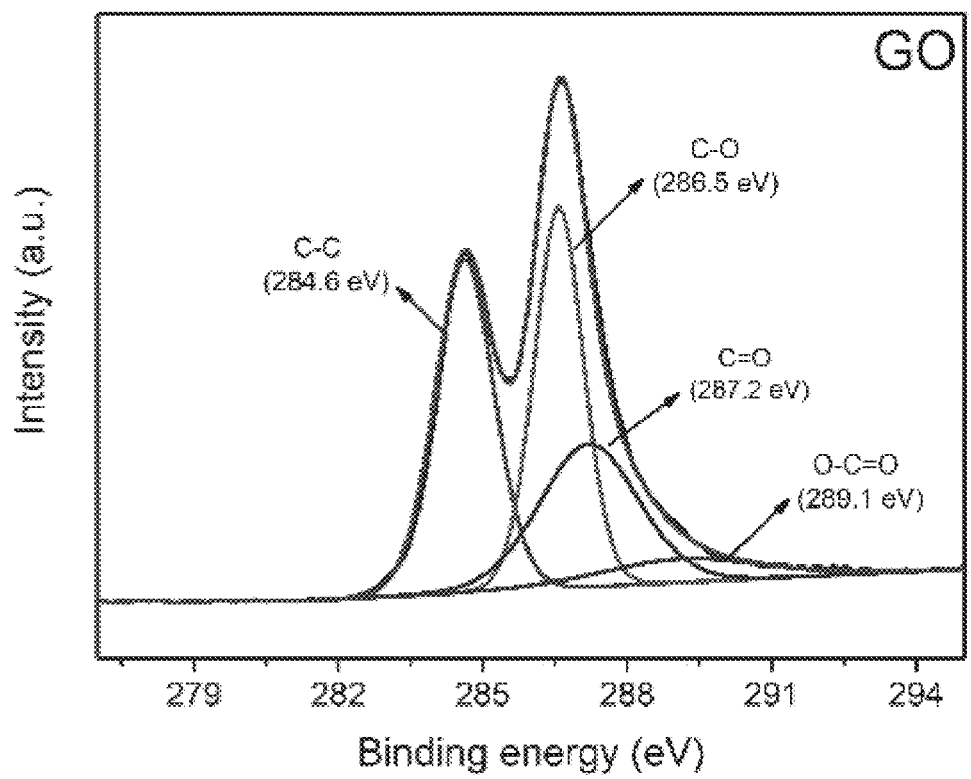
FIG. 13B shows the high resolution XPS C1s spectra of GO.
Figure 13C:
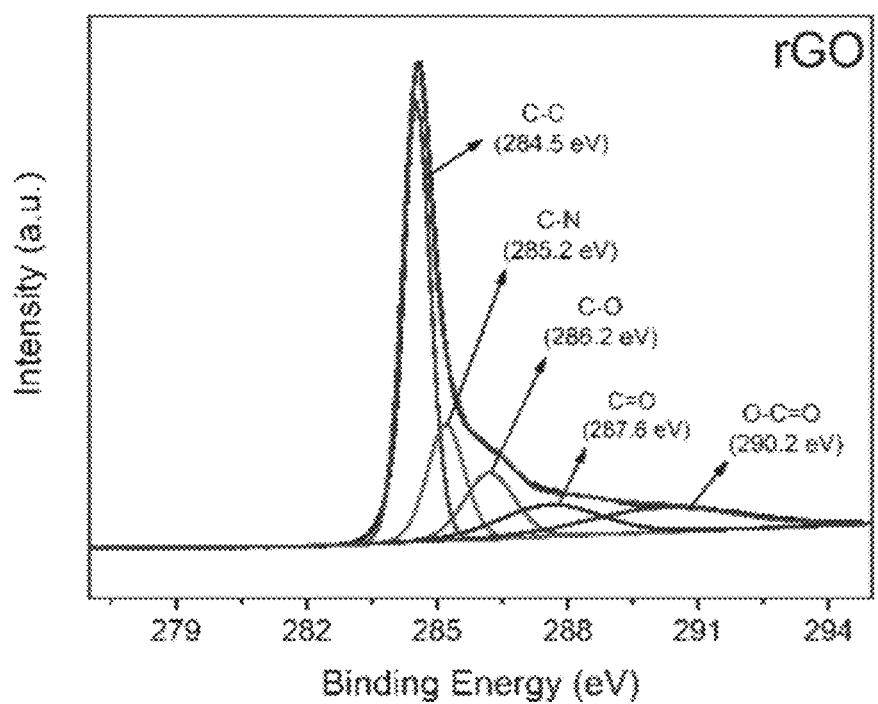
FIG. 13C shows the high resolution XPS C1s spectra of rGO.
Figure 13D:
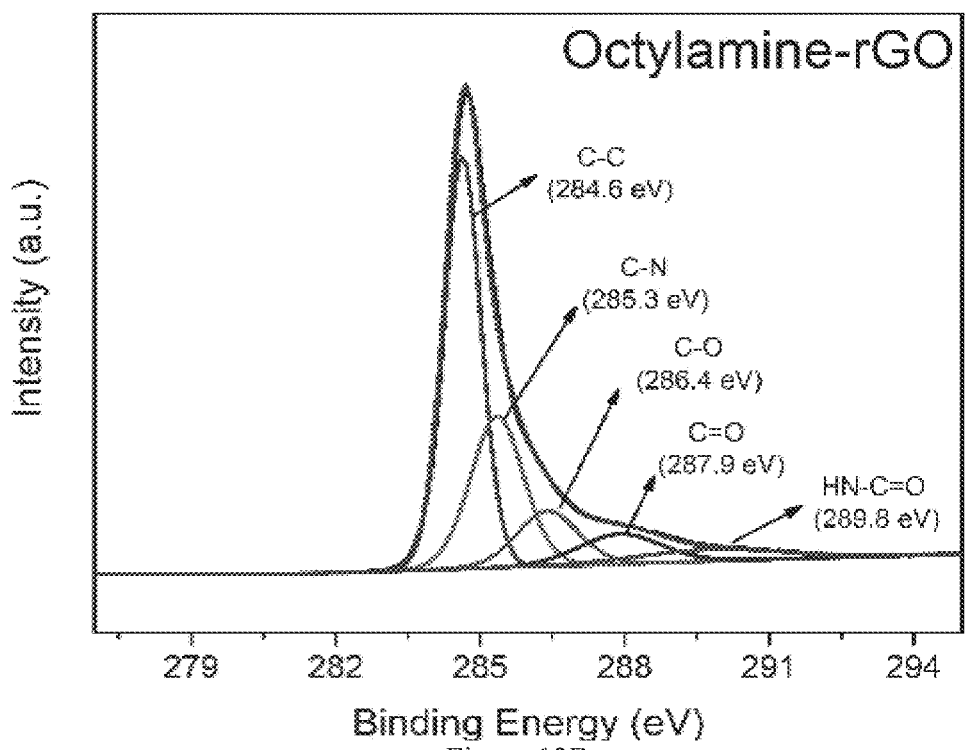
FIG. 13D shows the high resolution XPS C1s spectra of octylamine-rGO.

X-ray photoelectron spectrometry (XPS) was employed to study the surface properties on GO, rGO and octylamine-rGO. As shown in FIG. 13A, GO showed the strong peaks of C1s and O1s due to the oxygen-containing functional groups on the GO surface. Compared with GO, a weak peak of N1s and an increase in the intensity ratio of C1s/O1s were observed because of chemical reduction of GO. For octylamine-rGO, the reduction of GO and the covalent binding of octylamine also led to a stronger peak of N1s and an increase in the intensity ratio of C1s/O1s. High resolution XPS C1s was conducted to evaluate the chemical bonds in GO, rGO and octylamine-rGO (FIGS. 13B to D). The C1s peak of GO could be fitted into four curves, which were attributed to the non-oxygenated carbon skeleton (C—C, 284.6 eV) and the hydroxyl group (C—O, 286.5 eV), the carbonyl group (C═O, 287.2 eV) and the carboxyl group (O—C═O, 289.1 eV). In rGO, chemical reduction by hydrazine led to the weakened peaks of the oxygen-containing functional groups and the appearance of new C—N peak at 285.2 eV. Similarly, weaker peaks of the oxygen-containing functional groups were observed in octylamine-rGO, indicating the reduction of GO. Compared with rGO, the covalent bonds of octylamine on the surface of GO led to a stronger C—N peak at 285.3 eV in octylamine-rGO.

Figure 14:
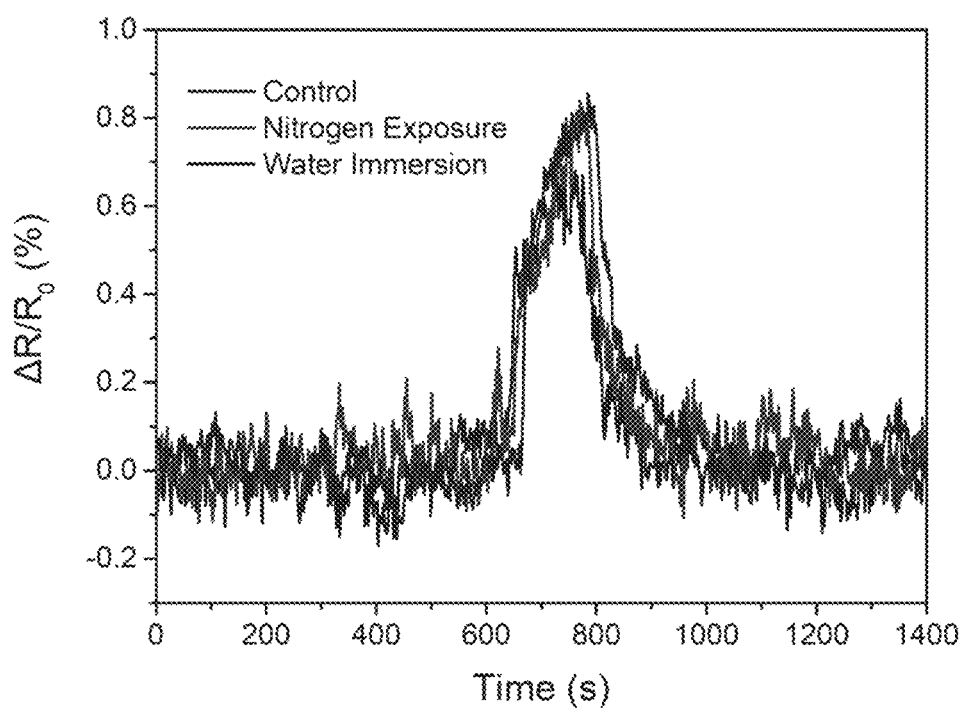
FIG. 14 shows the response of octylamine-rGO after 25 L/min nitrogen flow exposure for 30 min and after water immersion for 30 min.

The sensing properties of the functionalized rGO was investigated by constructing a prototype of chemiresistive electronic nose, which consisted of 9 pairs interdigitated electrodes arrays. rGO and eight different functionalized rGO were deposited on the interdigitated electrodes spots, respectively. Ethanol, 2-ethylhexanol, nonanal and ethylbenzene were chosen as the model VOCs analytes, which were suggested as the biomarkers of lung and liver cancers diseases.[15, 41-43] The sensing elements showed stable responses after 30 minutes strong nitrogen flow (25 L/min) or immersion in water, which indicated strong adhesiveness of the rGOs to the interdigitated electrodes during the experiments (FIG. 14).

Figure 15A:
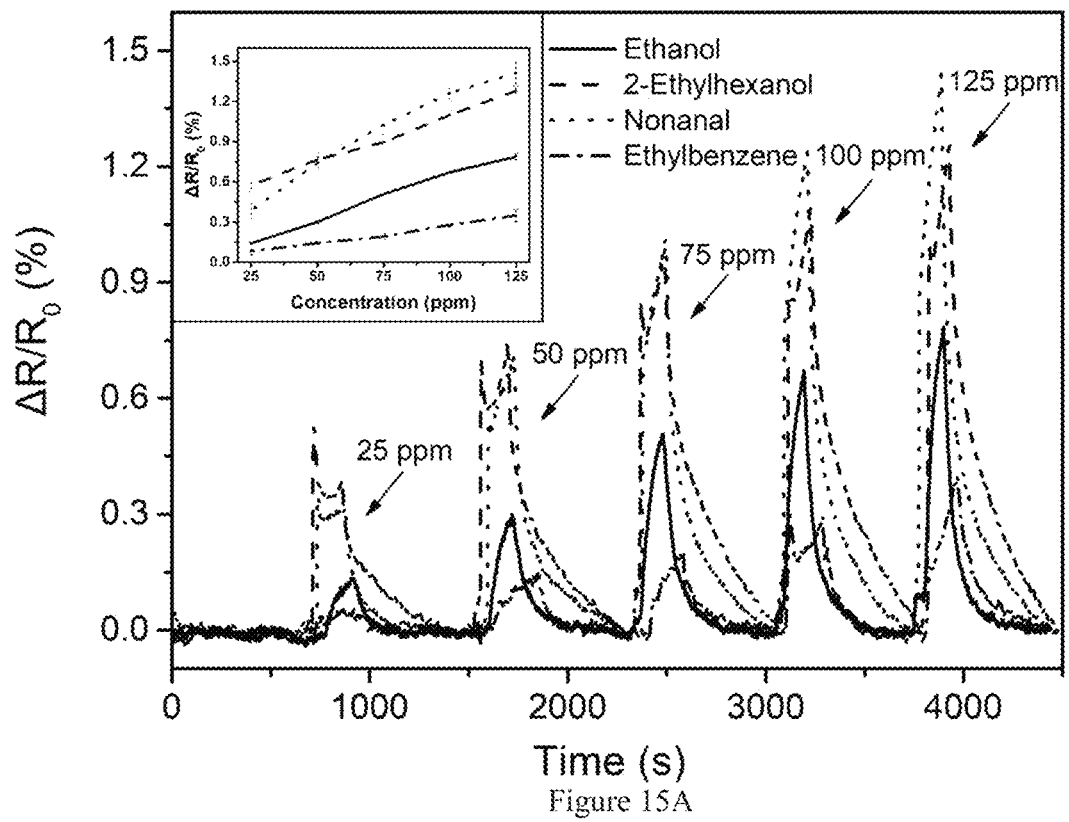
FIG. 15A shows the resistance response curves of octylamine-rGO to different VOCs (25-125 ppm).
Figure 15B:
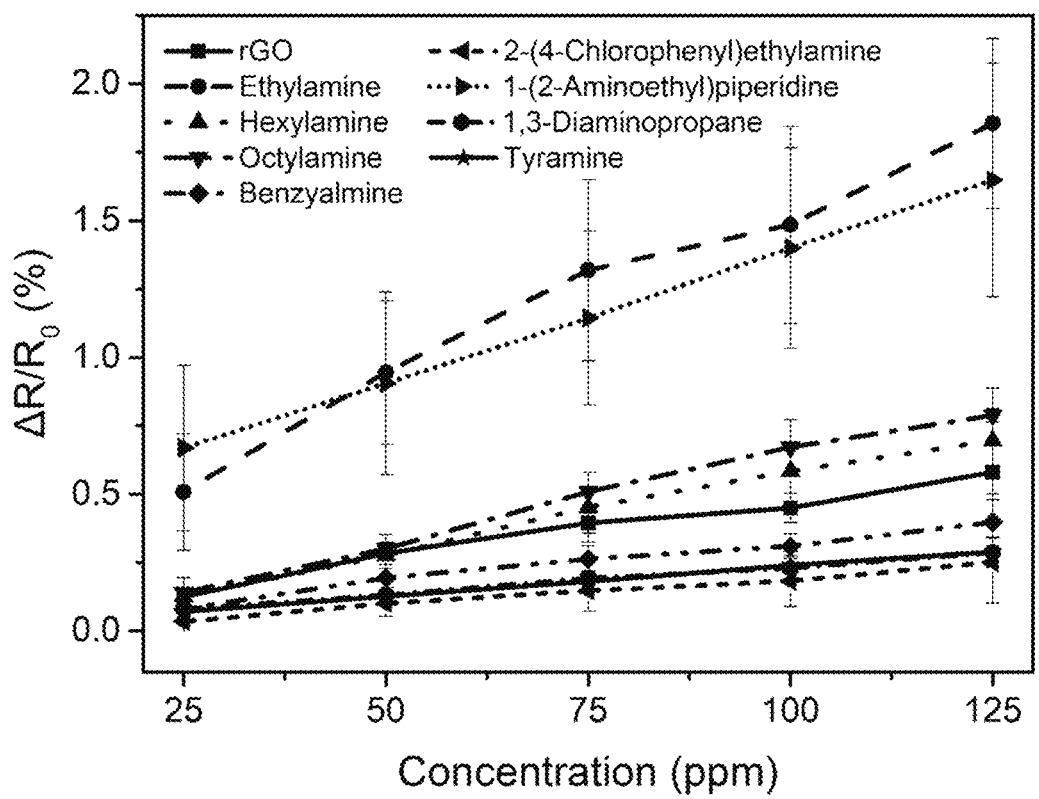
FIG. 15B shows the resistance response of nine sensing elements to different concentrations of ethanol.
Figure 15C:
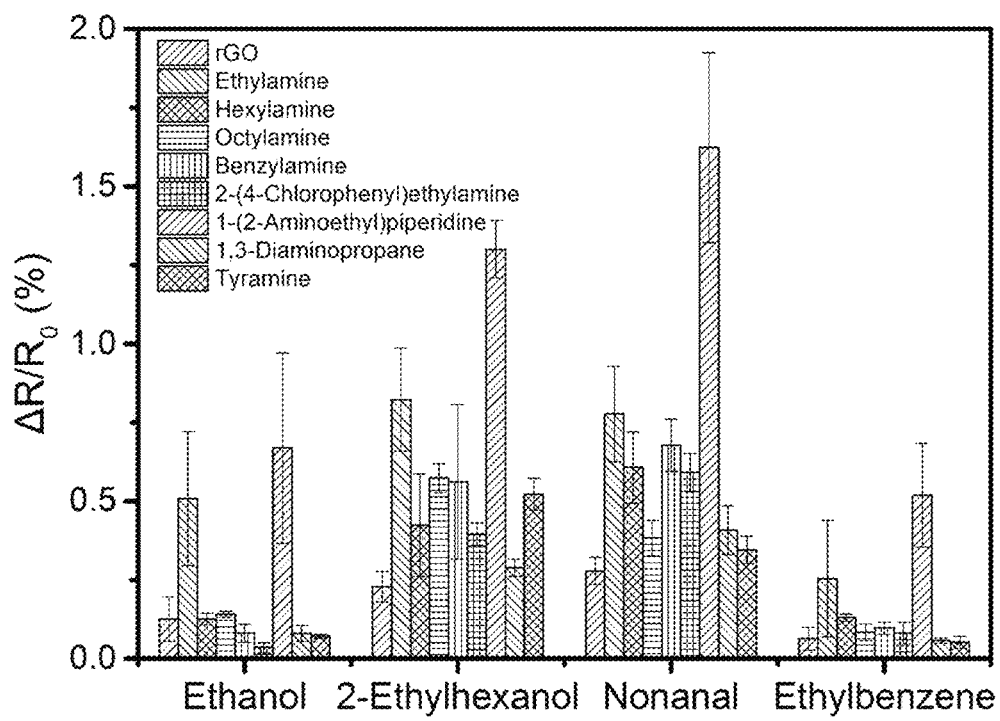
FIG. 15C shows the comparison of resistance responses of the electronic nose to the VOCs analytes at 25 ppm.
Figure 16:
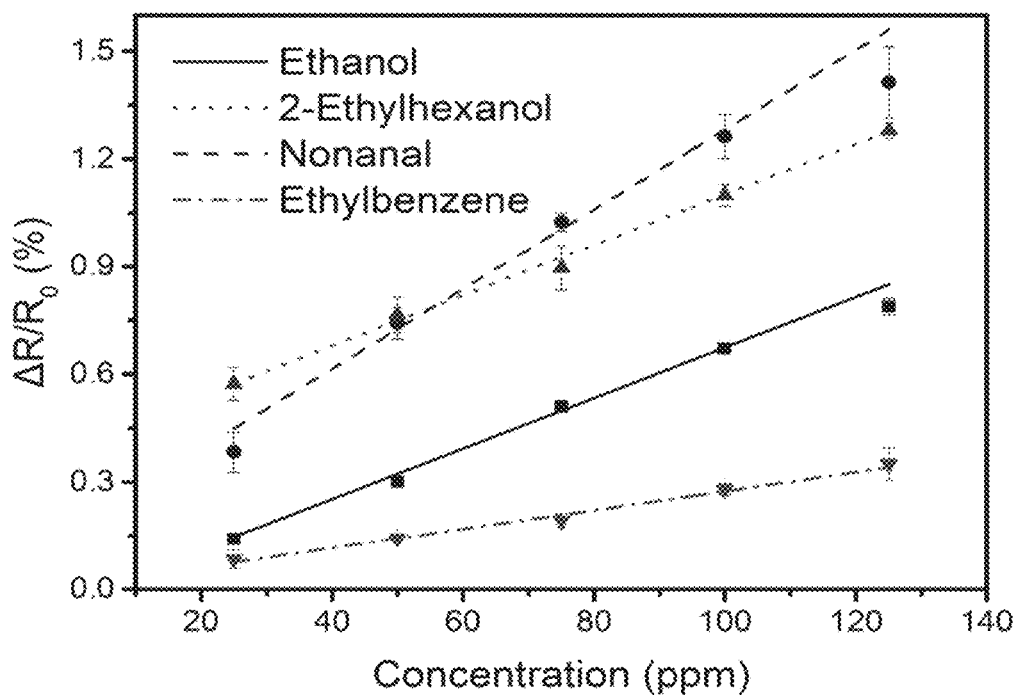
FIG. 16 shows the linear regression analysis on octylamine-rGO responses towards VOCs.
Figure 17A:
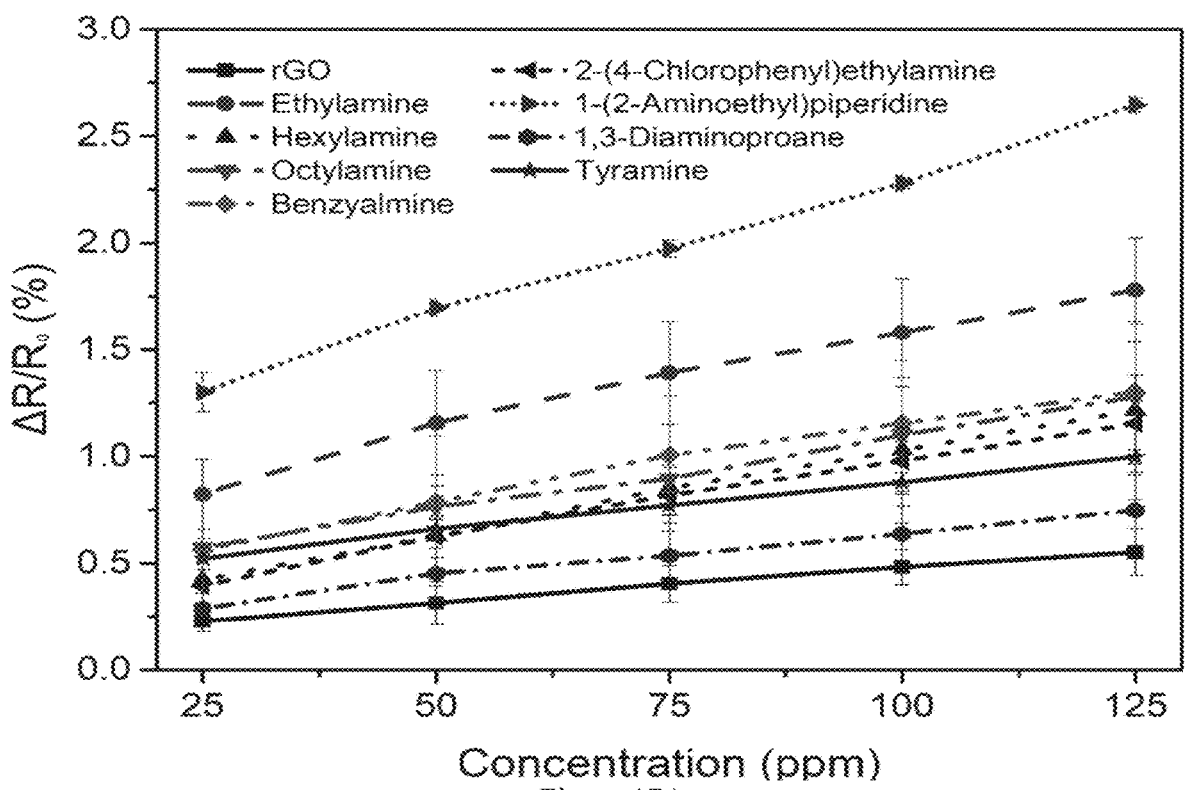
FIG. 17A shows the responses of rGO and functionalized rGO under the exposure of VOC biomarkers at different concentrations of 2-ethylhexanol.
Figure 17B:
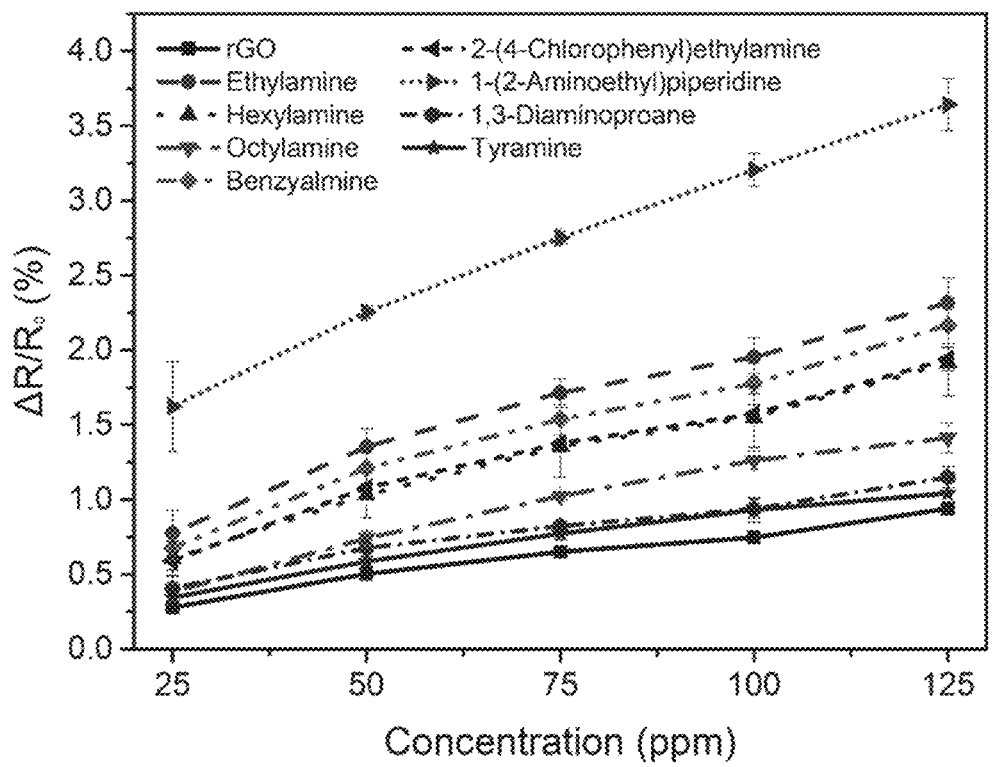
FIG. 17B shows the responses of rGO and functionalized rGO under the exposure of VOC biomarkers at different concentrations of nonanal.
Figure 17C:
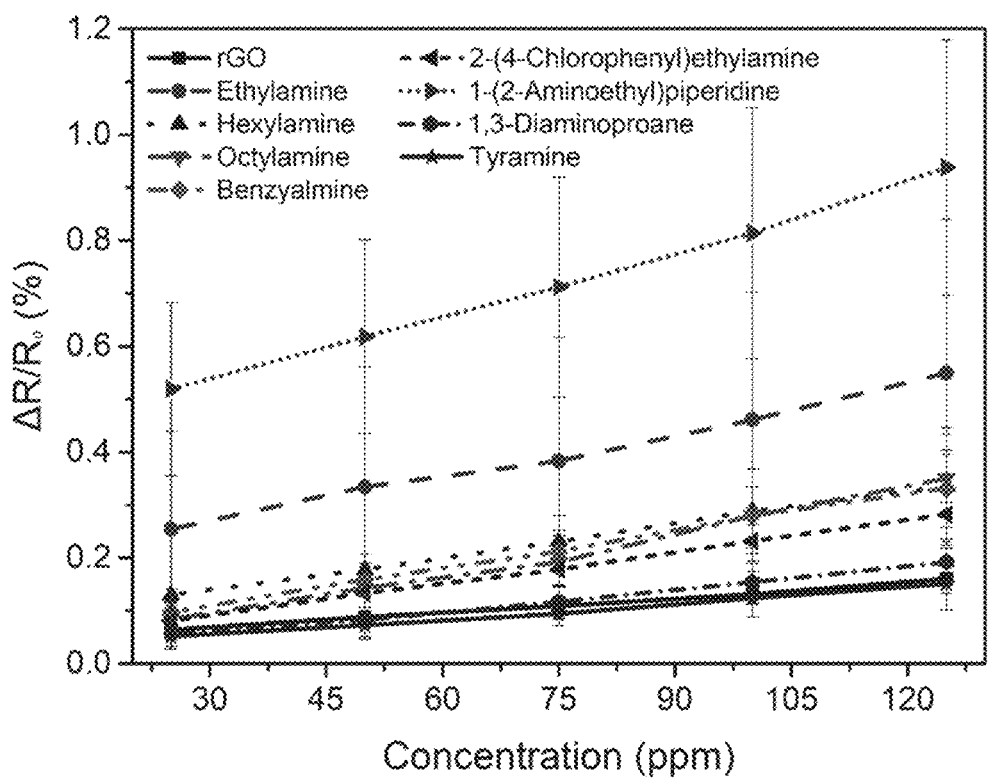
FIG. 17C shows the responses of rGO and functionalized rGO under the exposure of VOC biomarkers at different concentrations of ethylbenzene.
Figure 18A:
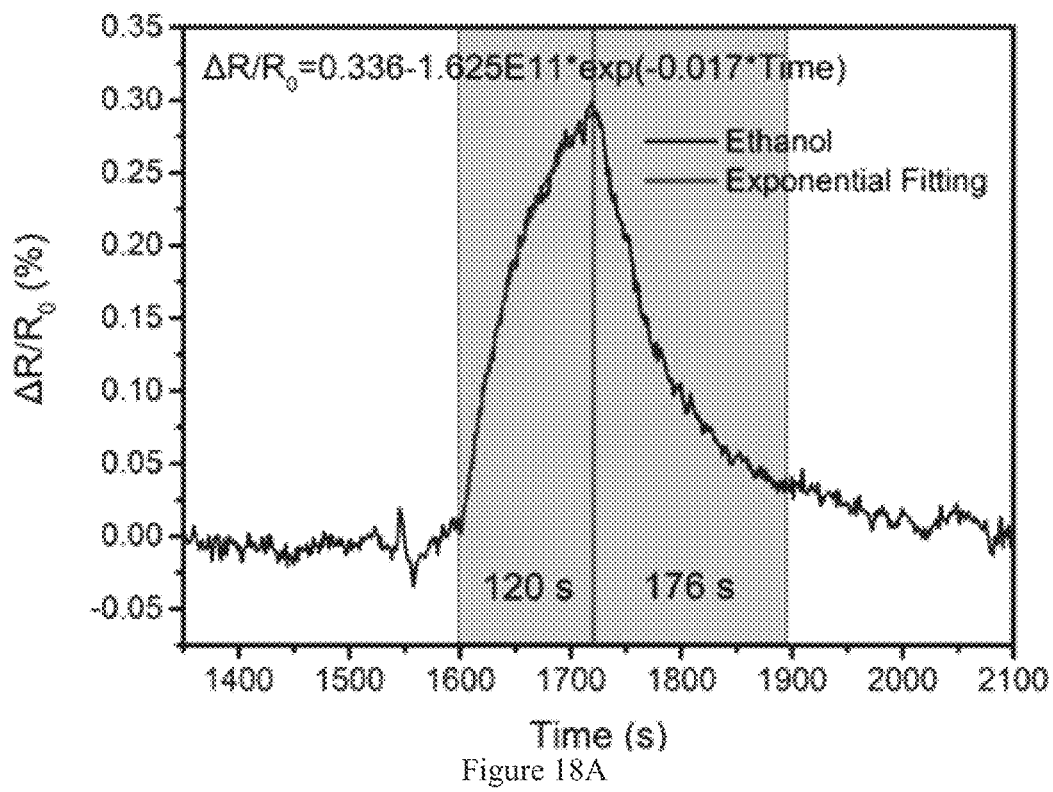
FIG. 18A shows the response and recovery curves of octylamine rGO under the exposure of 50 ppm the VOC biomarker, ethanol.
Figure 18B:
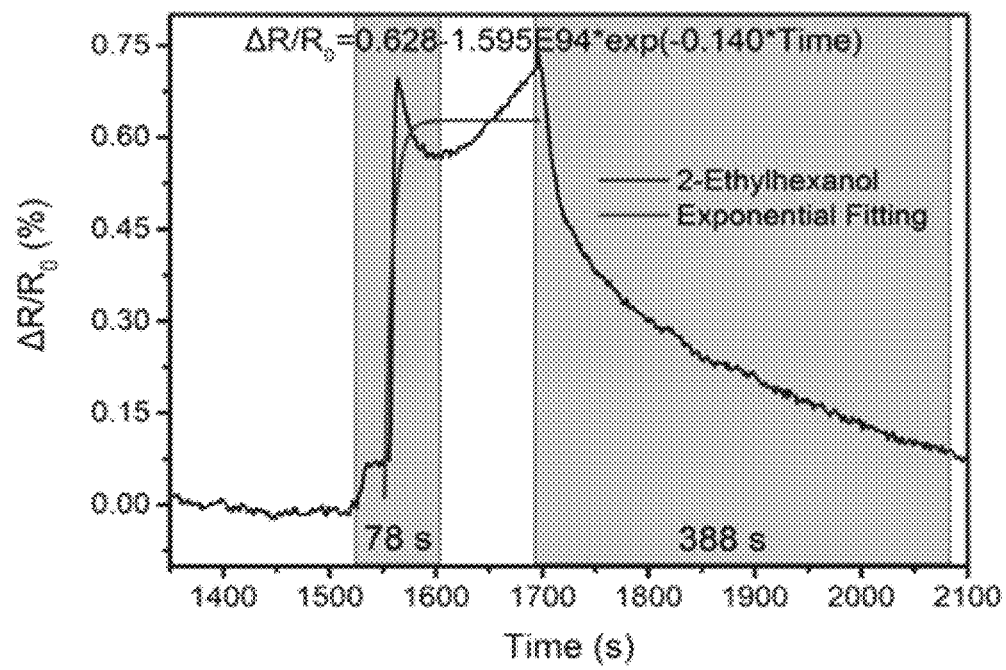
FIG. 18B shows the response and recovery curves of octylamine rGO under the exposure of 50 ppm the VOC biomarker, 2-ethylhexanol.
Figure 18C:
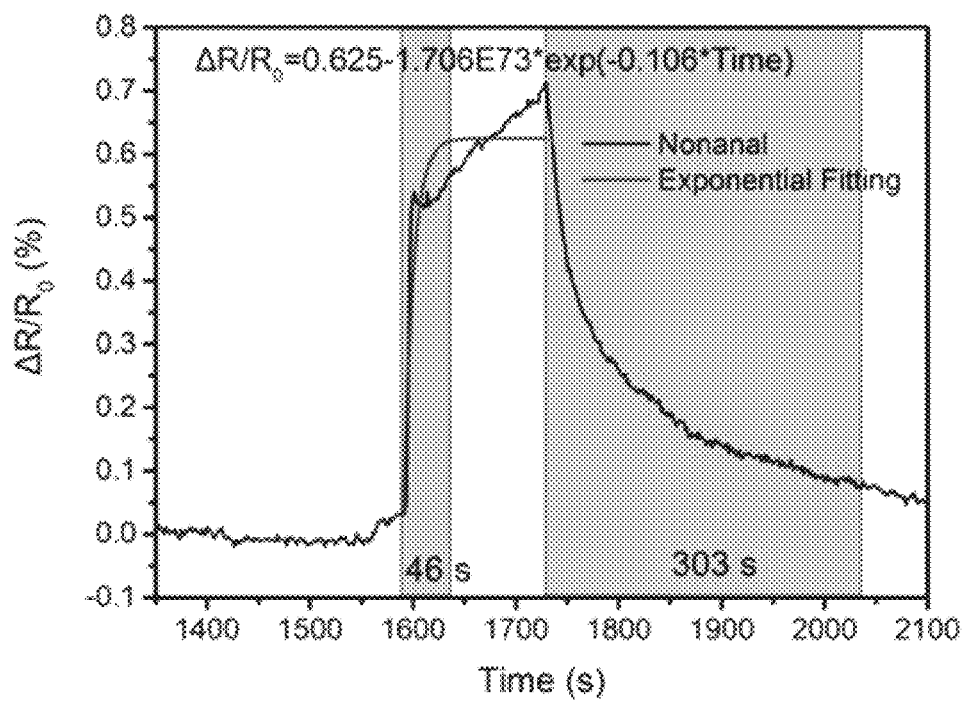
FIG. 18C shows the response and recovery curves of octylamine rGO under the exposure of 50 ppm the VOC biomarker, nonanal.
Figure 18D:
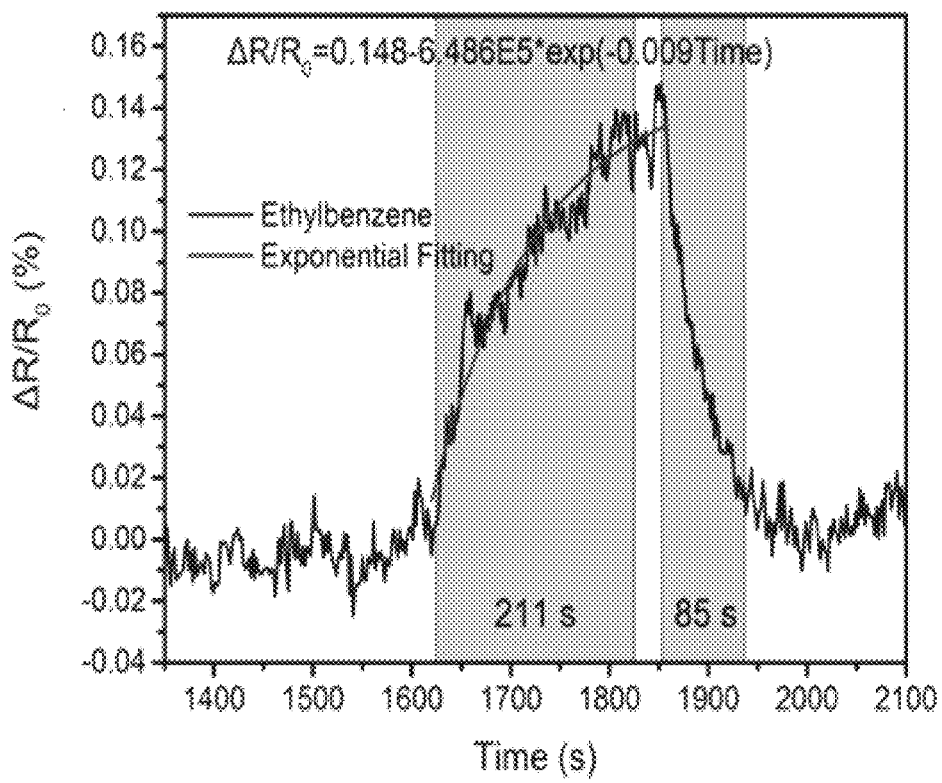
FIG. 18D shows the response and recovery curves of octylamine rGO under the exposure of 50 ppm the VOC biomarker, ethylbenzene.

The responses of the electronic nose to the VOCs analytes were studied by recording the resistance change of the sensor arrays. For the convenience of comparison, the response of the sensor was defined as $\Delta R/R_0$. $\Delta R$ was the resistance change of sensor when exposed to the VOCs analytes, and $R_0$ was the resistance value of the sensor under the nitrogen flow. The sensor arrays were exposed to different concentrations (25-125 ppm) of model VOCs analytes at room temperature for 2 minutes to record their resistance responses. Herein we chose octylamine-rGO as a representative example to demonstrate the sensing ability. Octylamine-rGO was exposed to the four model VOCs analytes at different concentrations (FIG. 15A). The four model VOCs led to different levels of resistance increases in octylamine-rGO. The resistance response had a linear relationship with the VOCs concentrations, which enabled the quantification of the VOCs analytes. Octylamine-rGO presented linear response increase with VOC concentration in linear regression analysis (FIG. 16 and Table 2). Sensitivity capabilities were different among the VOCs. Compared with ethylbenzene suffering poorer sensitivity, lower concentration could be detected for ethanol, 2-ethylhexanol and nonanal due to the strong response intensity level. FIG. 15B and FIG. 17 showed the distinct responses of different sensing materials to ethanol vapor at different concentrations. The introduction of the amine ligands influenced the interactions between the sensing materials and the VOCs analytes and led to different resistance responses among the materials. FIG. 15C further summarized the resistance responses of electronic nose to model VOCs analytes at 25 ppm. Each VOC analyte had a unique resistance response composition pattern from the nine sensing elements. The diversity of sensing materials provided the electronic nose with cross-reactive sensing ability and generated resistance response patterns from individual sensing materials. The resistance response patterns allow us to discriminate different complex VOCs. Compared with rGO, ethylamine-rGO and 1-(2-aminoethyl) piperidine-rGO showed stronger response intensity to the VOCs, while the other functionalized rGOs presented weaker response intensity. For all the sensing elements, the responses to 2-ethylhexanol and nonanal were stronger than those to ethanol and ethylbenzene. Most importantly, rGO and the functionalized rGO each showed unique response selectivity to the VOCs biomarkers, and each VOC produced a unique response pattern.

TABLE 2

Summary of linear regression analysis on octylamine-rGO responses towards VOCs.

| VOC species | Ethanol | 2-Ethylhexanol | Nonanal | Ethylbenzene |
|---|---|---|---|---|
| Intercept/$10^{-2}$ | −2.9 | 39.8 | 17.1 | 1.0 |
| Slope/$10^{-3}$ | 7.0 | 7.0 | 11.1 | 2.6 |
| $R^2$ | 0.992 | 0.998 | 0.968 | 0.984 |

The distinct responses among the VOCs depended on the molecular interaction between the sensing materials and the VOCs molecules, which included the physisorption, chemisorption, charge transfer, and induced dipole scattering.[39, 49, 50] In this embodiment of the present invention, the functionalized amine ligands acted as the organic sensing layer, endowing the rGO with different surface properties, i.e., with different adsorption capacity against the VOCs molecules. The chemical diversity of the functionalized amine ligands, including alkyl chain, benzene ring, halogen and piperidine, affected the molecular interaction between the sensing materials and VOCs, allowing the sensor arrays to generate different responses to the VOCs analytes. For example, the polarity and molecular weight of the amine ligands allowed the sensing materials to present different van der Waals' forces with the VOCs, and the benzene-containing amine ligand would have the x-n interaction with the aromatic VOCs.

Figure 15D:
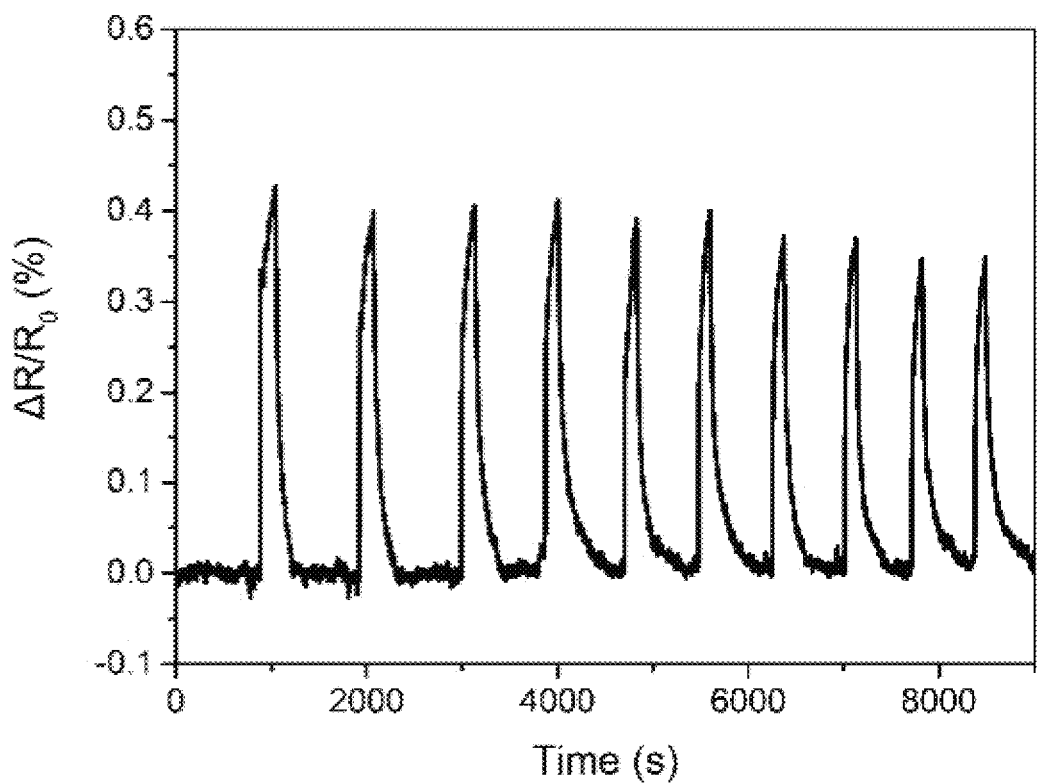
FIG. 15D shows the cycling stability of octylamine-rGO under multiple cycles of 25 ppm nonanal vapor exposure.
Figure 19A:
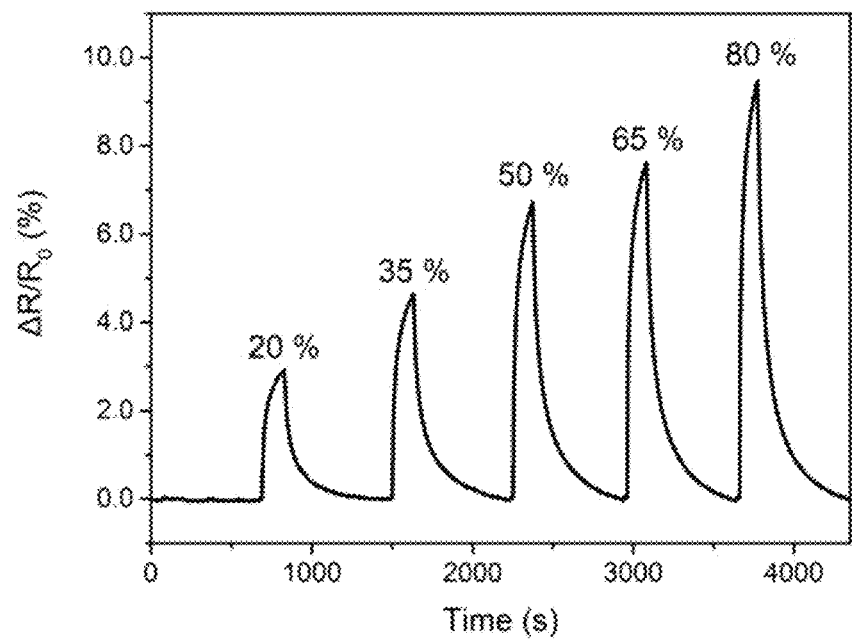
FIG. 19A shows the response of octylamine-rGO under the exposure of different humidity conditions.
Figure 19B:
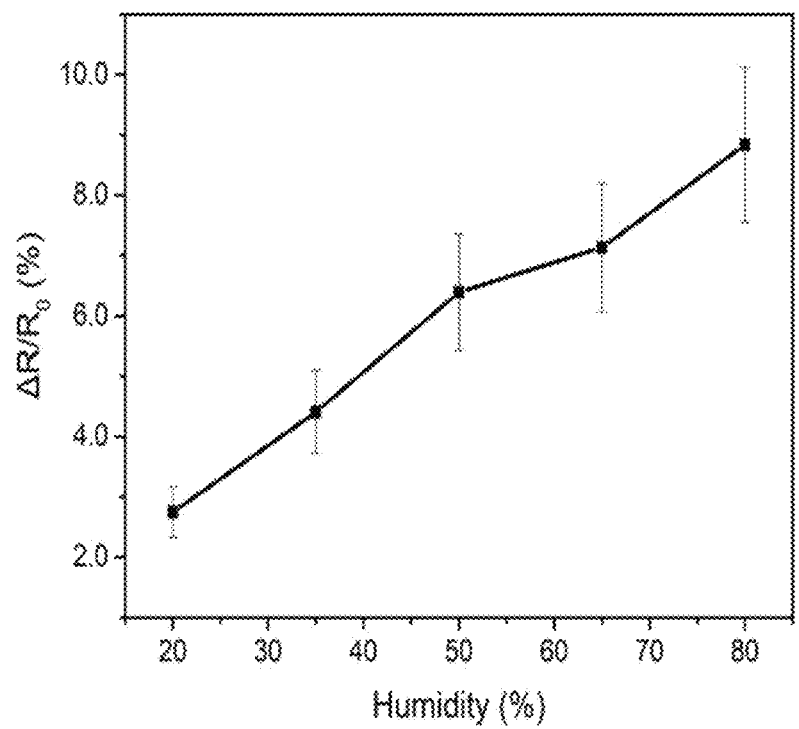
FIG. 19B shows the response curve of response of octylamine-rGO to humidity.

The stability of the gas sensor arrays with octylamine-rGO as the representative sensing material was also studied. The gas sensor was exposed to nonanal vapor at 25 ppm repeatedly, and nitrogen flow was applied to the gas chamber for 10 minutes so that the resistance curve could recover to the baseline. The response and recovery times of octylamine-rGO was measured with the help of exponential fitting (FIG. 18). As shown in Table 3, the response time was 61-200 s, and the recovery times was 97-416 s. The stability and humidity responses of octylamine-rGO were also investigated. FIG. 15D showed the resistance response of octylamine-rGO for 10 cycles of 25 ppm nonanal vapor exposures. Octylamine-rGO showed stable resistance response during the total 10 cycles, with negligible signal intensity decrease. Octylamine-rGO also showed linear responses increase to humidity (FIG. 19).

TABLE 3

Response and recovery times of octylamine-rGO under the exposure of 50 ppm VOC biomarkers

| | Response time (s) | Recovery time (s) |
|---|---|---|
| Ethanol | 124 ± 4 | 176 ± 11 |
| 2-Ethylhexanol | 79 ± 2 | 416 ± 25 |
| Nonanal | 61 ± 13 | 298 ± 21 |
| Ethylbenzene | 200 ± 9 | 97 ± 12 |

Figure 20A:
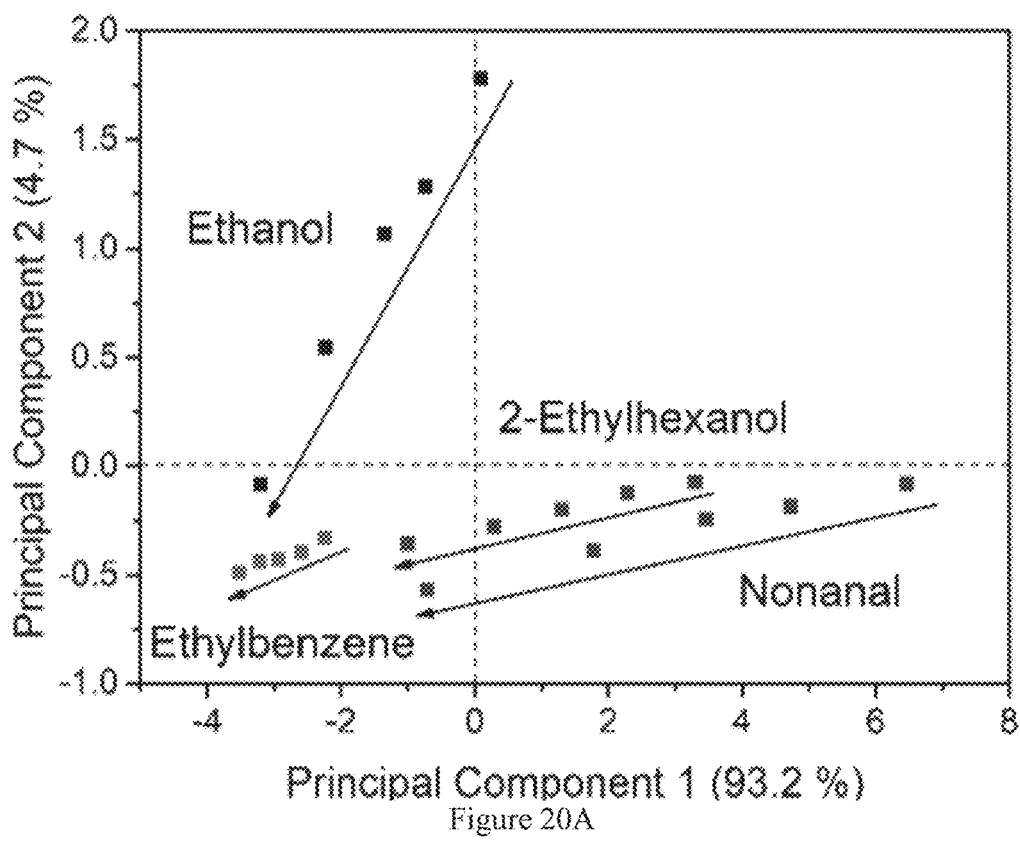
FIG. 20A shows PCA plot from the electronic nose in response to VOCs analytes at different concentrations.

The identification and discrimination of VOCs was critical for the function of the gas sensor. To evaluate the VOCs recognition performance of the electronic nose, we used PCA to analyze the resistance responses to model VOC analytes. PCA was an orthogonal linear transformation to project the data from a high dimensional one to a low dimensional one such that the variance of the projected data was maximized.[34, 38] The data was based on the peak resistance responses from rGO and eight different functionalized rGO, and we included five different concentrations of the VOCs from 25 ppm to 125 ppm. The parameters of PCA were summarized in Table 4-7. The PCA pattern of the electronic nose in response to four VOCs analytes at different concentrations was shown in FIG. 20A. After the dimension reduction, the first two principal components (PC 1-2) showed the variance contribution of 93.2% and 4.7%, with a high cumulative variance of 97.9%. As shown in FIG. 20A, four VOCs analytes (ethanol, 2-ethylhexanol, nonanal and ethylbenzene) with five different concentrations could be differentiated with others, and the arrows in the FIG. 20A indicated the decrease in the concentration of the VOCs analytes. To further demonstrate the performance of the electronic nose, we performed 3 parallel trials of experiments for four VOCs analytes discrimination at 100 ppm, and the result of PCA pattern was shown in FIG. 20B. The first two PCs accounted for a cumulative variance of 96.3%. Each VOCs analyte in the PCA formed a cluster, and the clusters could be well separated from the others. The sensor arrays demonstrated the capability to identify and discriminate the VOCs vapor and quantitatively measure the target analyte.

TABLE 4

The coefficients of PC1 and PC2 in PCA FIG. 20A.

|  | Coefficients of PC1 | Coefficients of PC2 |
|---|---|---|
| rGO | 0.326 | 0.455 |
| Ethylamine-rGO | 0.314 | 0.635 |
| Hexylamine-rGO | 0.343 | −0.023 |
| octylamine-rGO | 0.335 | 0.185 |
| benzylamine-rGO | 0.337 | −0.313 |
| 2-(4-chlorophenyl)ethylamine-rGO | 0.333 | −0.376 |
| 1-(2-aminoethyl)piperidine-rGO | 0.344 | −0.034 |
| 1,3-diaminopropane-rGO | 0.340 | −0.233 |
| tyramine-rGO | 0.326 | −0.246 |

TABLE 5

Figure 20B:
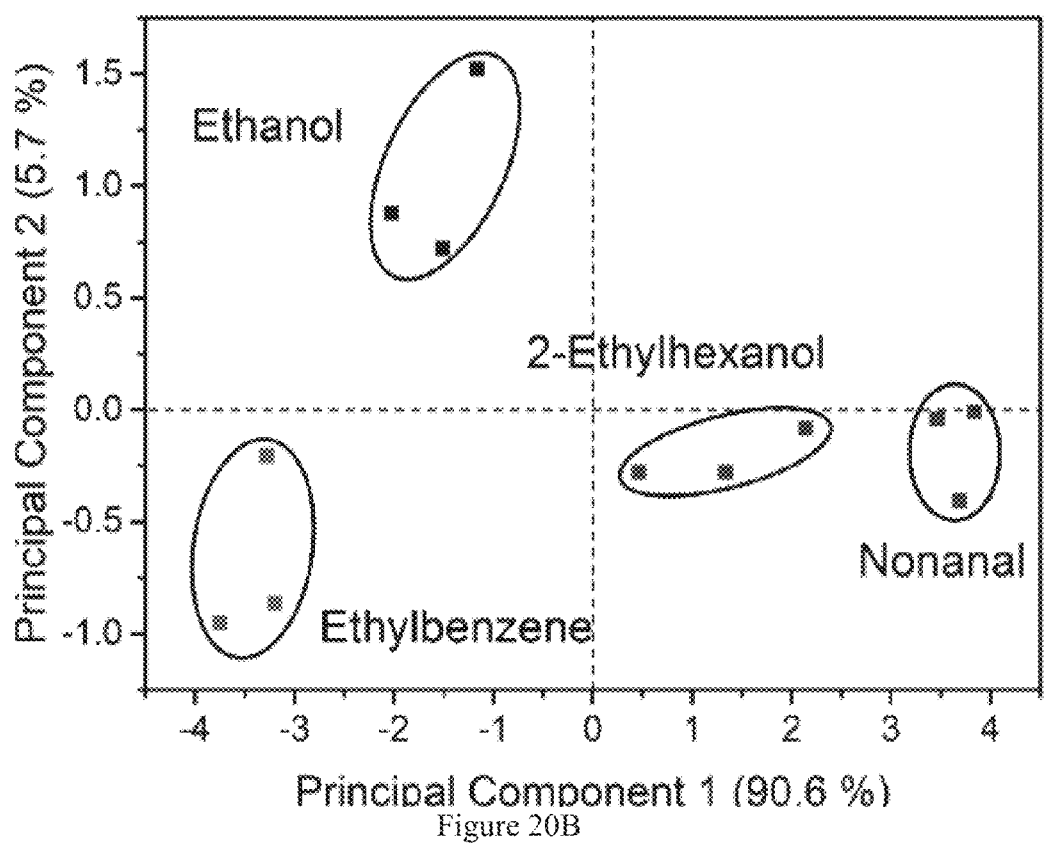
FIG. 20B shows PCA plot from parallel experiments of electronic nose in response to VOCs analytes at 100 ppm.

The coefficients of PC1 and PC2 in PCA of FIG. 20B.

|  | Coefficients of PC1 | Coefficients of PC2 |
|---|---|---|
| rGO | 0.328 | 0.408 |
| Ethylamine-rGO | 0.301 | 0.690 |
| Hexylamine-rGO | 0.340 | 0.000 |
| octylamine-rGO | 0.340 | 0.108 |
| benzylamine-rGO | 0.340 | −0.295 |
| 2-(4-chlorophenyl)ethylamine-rGO | 0.334 | −0.381 |
| 1-(2-aminoethyl)piperidine-rGO | 0.344 | 0.027 |
| 1,3-diaminopropane-rGO | 0.340 | −0.239 |
| tyramine-rGO | 0.331 | −0.237 |

TABLE 6

Figure 20C:
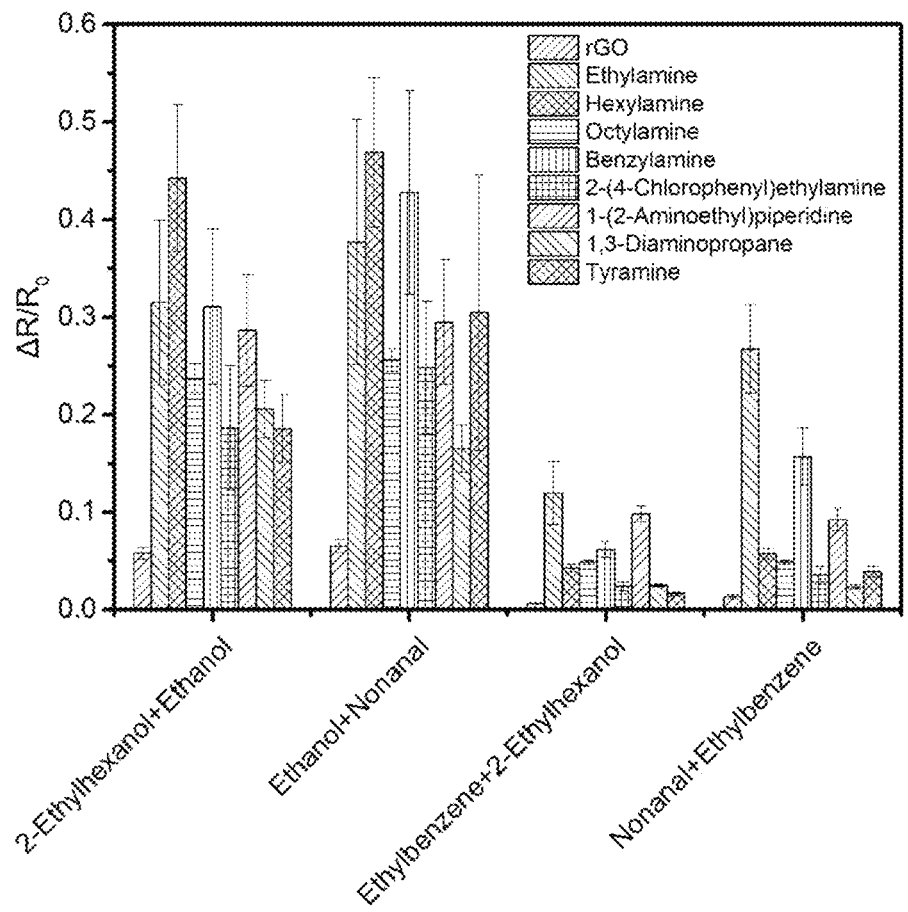
FIG. 20C shows responses of the electronic nose to four 1:1 saturated binary VOC mixtures.
Figure 20D:
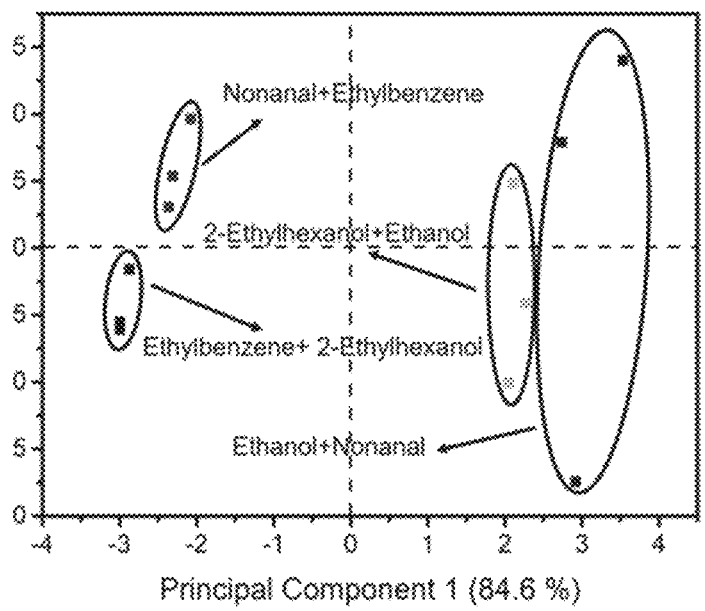
FIG. 20D shows PCA plot of the electronic nose for 1:1 saturated binary VOC mixtures.
Figure 21A:
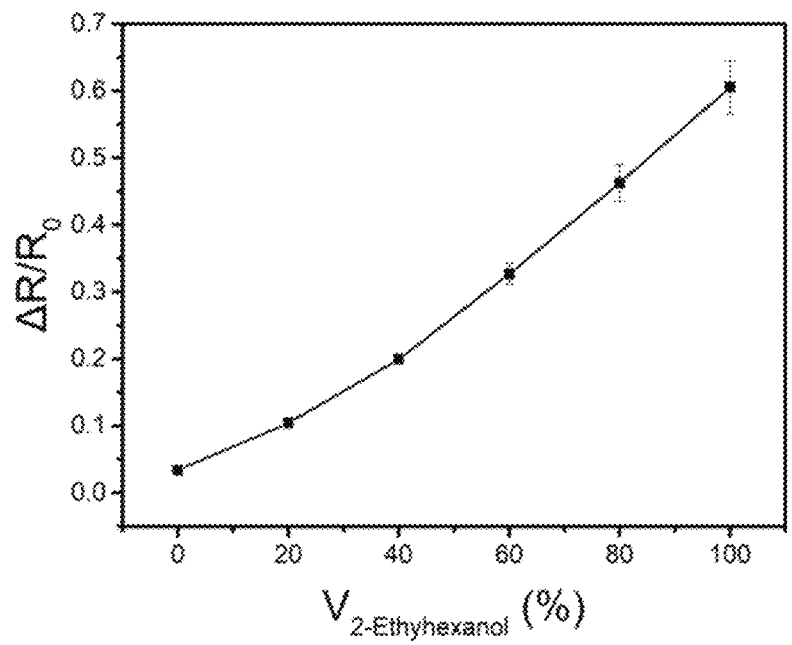
FIG. 21A shows the responses of octylamine-rGO under the exposures of different compositions of saturated binary VOC mixtures, 2-ethylhexanol and ethanol.
Figure 21B:
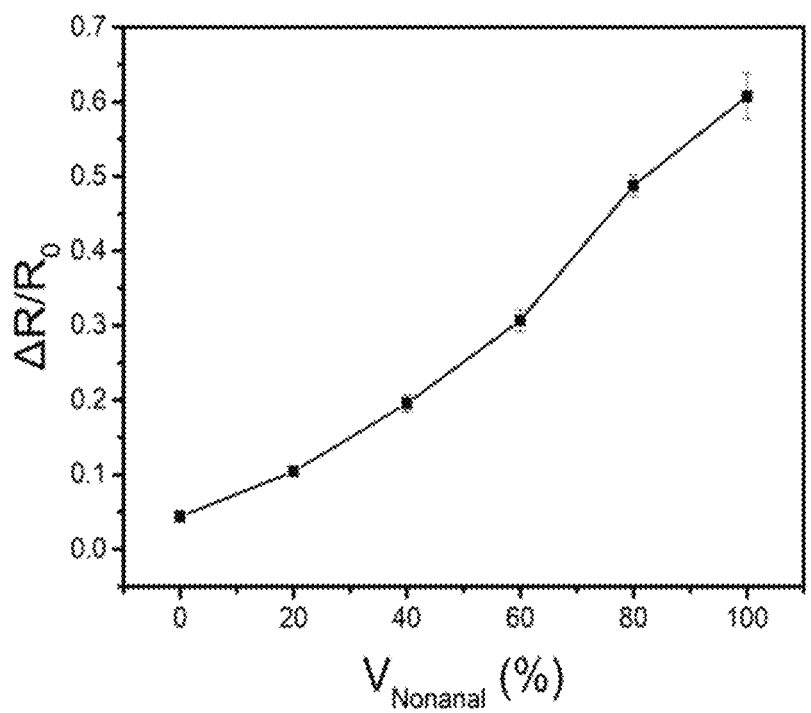
FIG. 21B shows the responses of octylamine-rGO under the exposures of different compositions of saturated binary VOC mixtures, ethanol and nonanal.
Figure 21C:
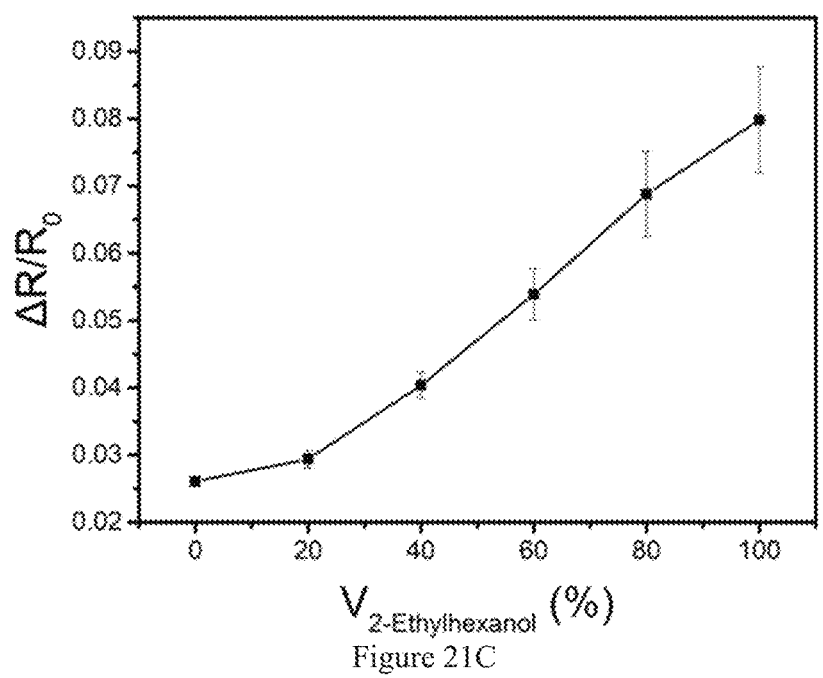
FIG. 21C shows the responses of octylamine-rGO under the exposures of different compositions of saturated binary VOC mixtures, ethylbenzene and 2-ethylhexanol.
Figure 21D:
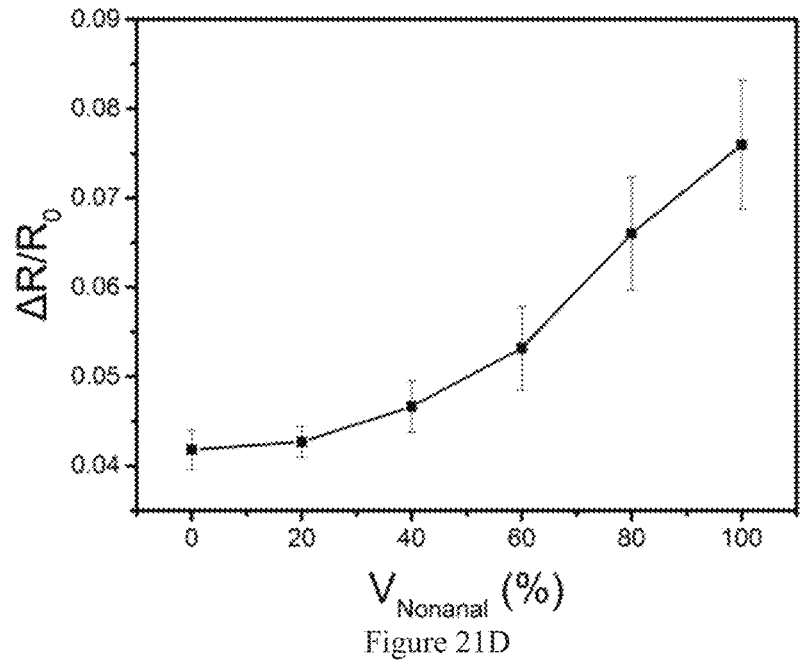
FIG. 21D shows the responses of octylamine-rGO under the exposures of different compositions of saturated binary VOC mixtures, nonanal and ethylbenzene.

The coefficients of PC1 and PC2 in PCA of FIG. 20D.

|  | Coefficients of PC1 | Coefficients of PC2 |
|---|---|---|
| rGO | 0.359 | 0.045 |
| Ethylamine-rGO | 0.265 | 0.722 |
| Hexylamine-rGO | 0.356 | −0.023 |
| octylamine-rGO | 0.359 | −0.088 |

TABLE 6-continued

The coefficients of PC1 and PC2 in PCA of FIG. 20D.

|  | Coefficients of PC1 | Coefficients of PC2 |
|---|---|---|
| benzylamine-rGO | 0.333 | 0.259 |
| 2-(4-chlorophenyl)ethylamine-rGO | 0.339 | 0.220 |
| 1-(2-aminoethyl)piperidine-rGO | 0.332 | −0.414 |
| 1,3-diaminopropane-rGO | 0.336 | −0.249 |
| tyramine-rGO | 0.310 | −0.347 |

TABLE 7

Figure 22:
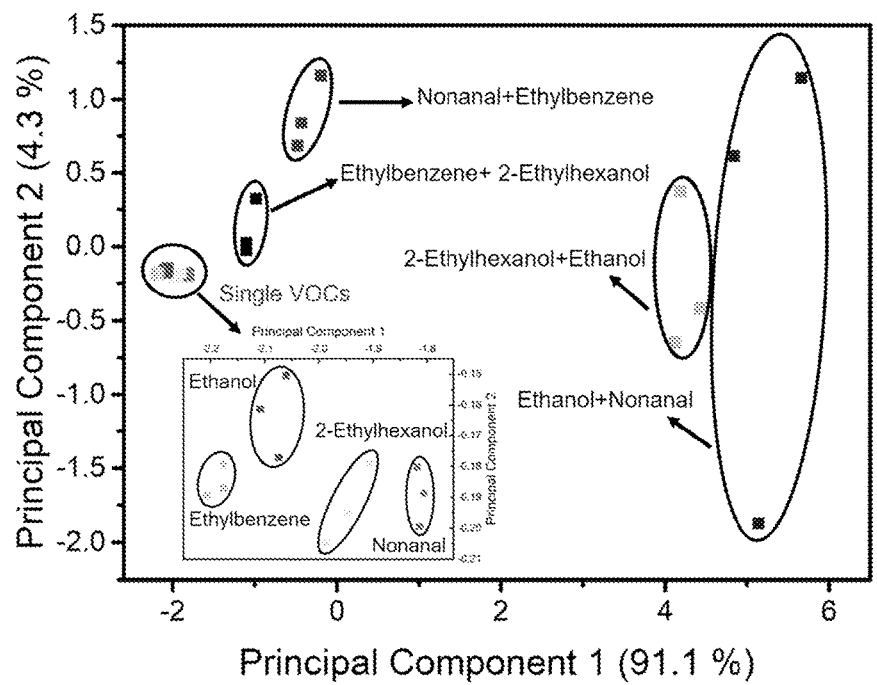
FIG. 22 shows the PCA plot of electronic nose for 100 ppm single VOCs and 1:1 saturated binary VOC mixtures.

The coefficients of PC1 and PC2 in PCA of FIG. 22

|  | Coefficients of PC1 | Coefficients of PC2 |
|---|---|---|
| rGO | 0.345 | −0.005 |
| Ethylamine-rGO | 0.306 | 0.714 |
| Hexylamine-rGO | 0.344 | −0.068 |
| octylamine-rGO | 0.348 | −0.066 |
| benzylamine-rGO | 0.335 | 0.290 |
| 2-(4-chlorophenyl)ethylamine-rGO | 0.334 | 0.171 |
| 1-(2-aminoethyl)piperidine-rGO | 0.336 | −0.258 |
| 1,3-diaminopropane-rGO | 0.334 | −0.253 |
| tyramine-rGO | 0.316 | −0.488 |

Two saturated VOC vapors, 2-ethylhexanol and nonanal, were mixed at different ratios to prepare the VOC mixtures for further investigation. The sensing elements showed ratio-wise responses to VOC mixtures (FIG. 21). The responses of the electronic nose to four binary VOC mixtures at the mixing ratio of 1:1 were summarized in FIG. 20C. PCA was used to analyze the VOC mixtures responses, and each binary VOC mixture formed a cluster and were well separated from each other (FIG. 20D), demonstrating the discriminating power of the electronic nose towards VOC mixtures. Furthermore, PCA was used to analyze single VOCs and binary VOC mixtures together, which were also differentiate with each other in PCA plot (FIG. 22).

After evaluating performance of the electronic nose, the present invention was compared with the electronic noses in previous reported works. Semiconductor metal oxides, conductive polymer and carbon materials are widely used as the sensing materials in the development of electronic noses (Table 8). Metal oxides based electronic noses have high sensitivity but generally operate at high temperature and pose difficulties for library building[54, 61]. Conductive polymers based electronic noses have good mechanic properties and good sensitivity at room temperature. However, the electronic noses are highly susceptible to ambient environmental humidity[51, 52]. For the electronic noses in previously reported works, physicaldopingandhybridcompositionstuningarethemostpopularapproachesforthe library building due to the simplicity. In the present invention, one distinct advantage is the chemistry of rGO, which allowed building of a functionalized rGO library through facile one-step synthesis, and the electronic nose showed high sensitivity as low as 25 ppm at room temperature.

TABLE 8

Sensing properties summary of the previously reported electronic noses.

| Sensing material | Library building method | Working temperature | Sensitivity | Reference |
|---|---|---|---|---|
| WO$_3$ | Nanoparticle doping | 300-450° C. | 0.1-5 ppm | 53 |
| In$_2$O$_3$ | Layer thickness | 340° C. | 100 ppm | 7 |
| ZnO—MnO$_2$ | Components ratio tuning | 320° C. | 100 ppm | 54 |
| Diketopyrrolopyrrole | polymer derivates | — | 10% saturated vapor | 55 |
| Poly(2-phenyl-1,4-xylylene) | Porphyrin doping | 35° C. | 5-36% | 56 |
| rGO | Ionic liquid doping | Room temperature | 20 ppm | 38 |
| rGO | rGO thickness | Room temperature | 500-1500 ppm | 57 |
| Single walled carbon nanotubes | Porphyrin doping | Room temperature | 50-100% | 34 |
| rGO | Amine chemical functionalization | Room temperature | 25 ppm | The present invention |

The electronic nose was expected to be useful in applications such as analysis of food products and cosmetic products. However, translating the current research into the clinic diagnosis still faces several challenges. Human breath has complicated compositions with high humidity and many interfering chemical species. The trace concentration of some VOC biomarkers in human breath is another challenge. The electronic nose in the present invention still needs to be improved to address the complexity of breath analysis. More functionalized species should be screened to enhance the sensitivity to ppb level. Efficient algorithm should be developed to optimize the data analysis, which should benefit from the construction of databases containing large number of breath sample analysis.

In conclusion, a library of functionalized rGO with different amine ligands was prepared via covalent linkage. The functionalized rGO presented the rough and wrinkled morphology, and the characterization results demonstrated the reduction of GO and the successful introduction of amine ligands via covalent bonds. The simple functionalization method achieved the versatile functionalization on rGO, and the diversity of amine ligands endowed the functionalized rGO with different physical and chemical properties so that the cross-reactive sensing arrays in the electronic nose could produce different response patterns corresponding to different VOCs analytes. rGO and eight different functionalized rGO were used as the sensing elements to construct a new electronic nose for exhaled breath biomarkers identification and discrimination at room temperature. In the gas sensing experiments, four cancer-related biomarkers were chosen as the model VOCs analytes. The electronic nose showed linear resistance responses to four cancer-related model VOCs analytes at the concentration range from 25 ppm to 125 ppm and maintained stable resistance responses after 10 cycles of VOC exposures. PCA results demonstrated the successful discrimination of VOC biomarkers and binary VOC mixtures, which indicated the identification and discrimination ability of the electronic nose. The facile amine functionalization method provided a simple way to develop multifunctional and highly sensitive electronic nose in portable, inexpensive and fast diseases diagnosis, real-time human health monitoring and analyzing commercial products for quality control. To make the electronic nose applicable in clinical analysis of human breath, challenges including the ultralow concentrations of some VOC biomarkers and the high humidity in the human breath samples still needed to be overcame. To address the challenges, the rich chemistry of rGO shall be fully exploited and fully enhance the sensitivity and selectivity of the sensing materials.

Materials

Graphite (powder, <20 μm), ethylamine hydrochloride, hexylamine, octylamine, benzylamine, 2-(4-chlorophenyl) ethylamine, 1-(2-aminoethyl)piperidine, tyramine, hydrazine hydrate, DCC (N,N'-dicyclohexylcarbodiimide) were purchased from Sigma-Aldrich. 1,3-diaminopropane was from Aladdin.

Preparation of GO and rGO

Graphene oxide (GO) was prepared from graphite powder according to the modified Hummers' method.[40] 7.5 g K$_2$S$_2$O$_8$ and 7.5 g P$_2$O$_5$ were added into 36 mL concentrated H$_2$SO$_4$, and then 6 g graphite powder was added into the above H$_2$SO$_4$ solution. The suspension was stirred and heated in oil bath at 80° C. overnight. The suspension was diluted with deionized water slowly, and the mixture was filtered and washed by deionized water to neutral. The solid residue was dried in the drying oven and collected as the preoxidized graphite.

5 g preoxidized graphite powder, 2.5 g NaNO$_3$ and 120 mL concentrated H$_2$SO$_4$ were added and mixed together in an ice bath for 1 h. 15 g KMnO$_4$ was added slowly into the suspension, and the temperature of the mixture was kept below 20° C. The ice bath was removed after 2 h, and the suspension was kept stirring for 3 days. After 150 mL deionized water was added slowly into the suspension, the suspension was kept at 98° C. for 30 min. Further, 500 mL warm deionized water was added into the suspension, and 50 mL 30% H$_2$O$_2$ was finally added in to the suspension. The mixture was centrifuged and washed with 10% HCl, followed by washing with deionized water to become neutral in pH. The final GO product was obtained after drying in the oven.

The reduced graphene oxide (rGO) was prepared according to the published literatures.[58] 25 mg GO was dispersed in 100 mL deionized water by sonication for 1 h, and then 375 μL 30% ammonia and 50 μL hydrazine were added into the solution. The solution was kept at 95° C. with stirring for 1 h, and then the mixture was filtered and washed with deionized water.

Preparation of Functionalized rGO

Functionalized rGO was prepared according to the literature.[44-47] GO was reduced and functionalized with amine molecules by nucleophilic substitution and carbodiimide crosslinking. The amine molecules included ethylamine hydrochloride, hexylamine, octylamine, benzylamine, 2-(4-chlorophenyl)ethylamine, 1-(2-aminoethyl)piperidine, tyramine and 1,3-diaminopropane. Excess amine reagents and long reaction time were utilized to ensure the consistent functionalization results. Briefly, 100 mg GO, 3.75 mmol amine and 3.75 mmol DCC were added into 50 mL toluene with 4-dimethyl-aminopyridine as the catalyst, and the mixture was stirred at 80° C. for 2 days. For ethylamine hydrochloride, 7.50 mmol triethylamine was added due to the presence of hydrochlorides. The mixture was centrifuged and washed with toluene and ethanol.

Fabrication of the Electronic Nose

Figure 10A:
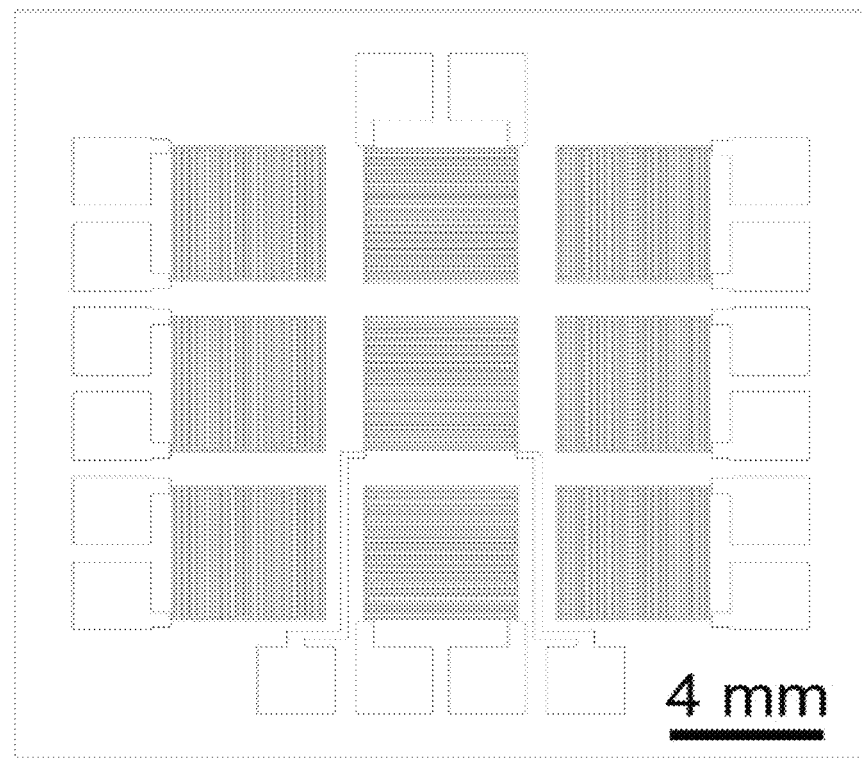
FIG. 10A shows the design of interdigitated electrodes arrays
Figure 10B:
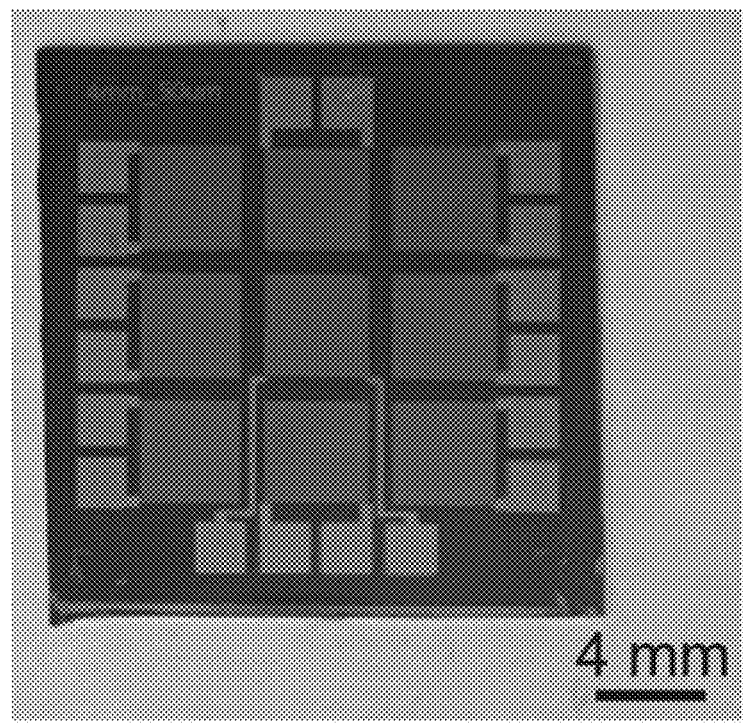
FIG. 10B shows a photo of the interdigitated electrodes arrays.

The electronic nose consisted of 9 pairs of interdigitated electrodes (FIG. 10), which was microfabricated on a commercial p-type silicon substrate with 500 nm $SiO_2$ insulated layer. Briefly, the interdigitated electrodes were patterned on the substrate by photolithography, and then 5 nm Cr layer and 100 nm Au layer were deposited on the substrate by evaporation. The width of the electrodes and the gap between two adjacent electrodes were both 50 μm.

The functionalized rGO was dispersed in dimethylformamide by ultrasonication to form 0.5 mg/mL solution. The solution was dropped on the interdigitated electrode, followed by drying under gentle nitrogen flow. The device was further dried overnight under ambient conditions to evaporate the solvent and form a sensing layer. For consistent performance of the electronic noses, the deposition amount of each functionalized rGO was controlled by monitoring the electrodes resistance.

rGO and eight functionalized rGO were included as the sensing elements to build the electronic nose. rGO and functionalized rGO were dispersed in dimethylformamide by ultrasonication and deposited on the interdigitated electrode, followed by drying under gentle nitrogen flow. The device was further dried overnight under ambient conditions to evaporate the solvent and form a sensing layer. For consistent performance of the electronic noses, we controlled the deposition amount of each functionalized rGO by monitoring the electrodes resistance.

Gas Sensing Studies

Figure 23A:
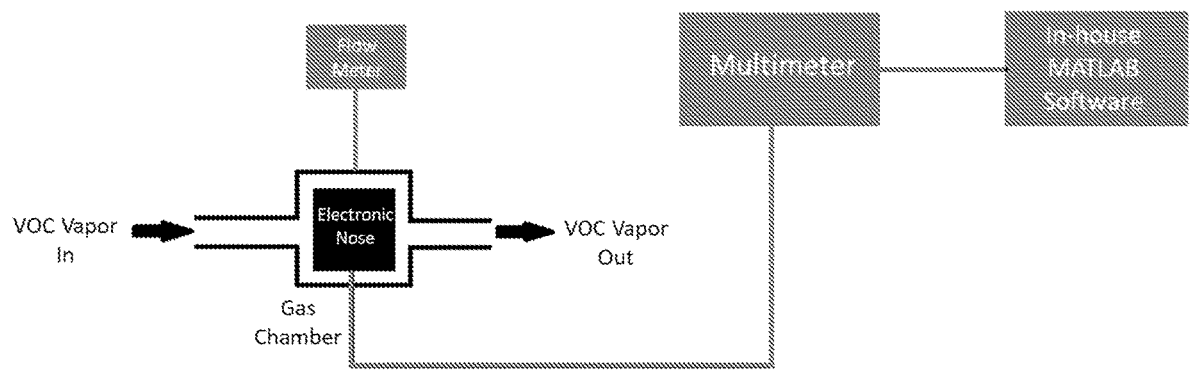
FIG. 23A shows the photo of the experimental setup for gas sensing studies.
Figure 23B:
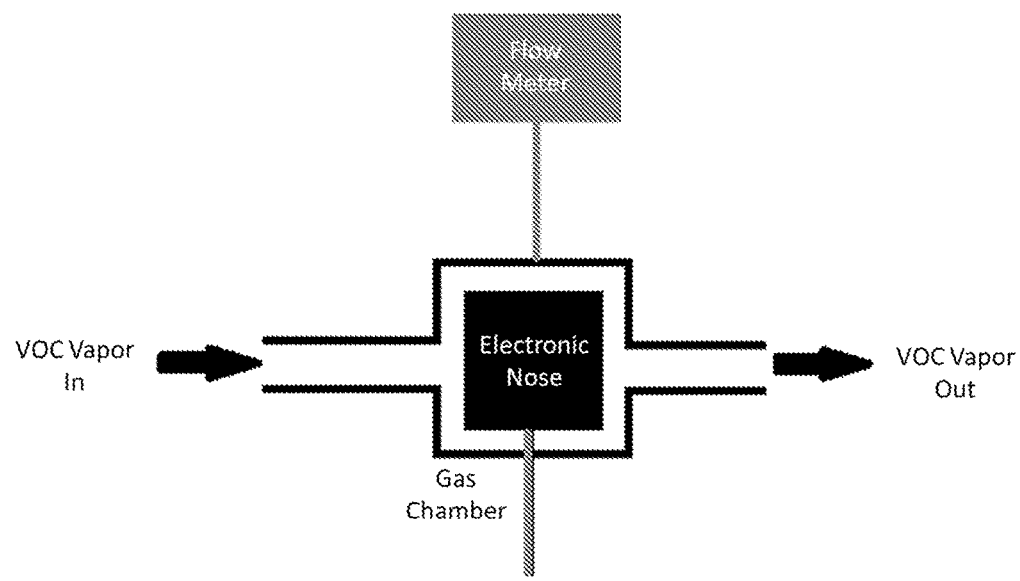
FIG. 23B shows the enlarged photo of the gas chamber for gas sensing studies.
Figure 24:
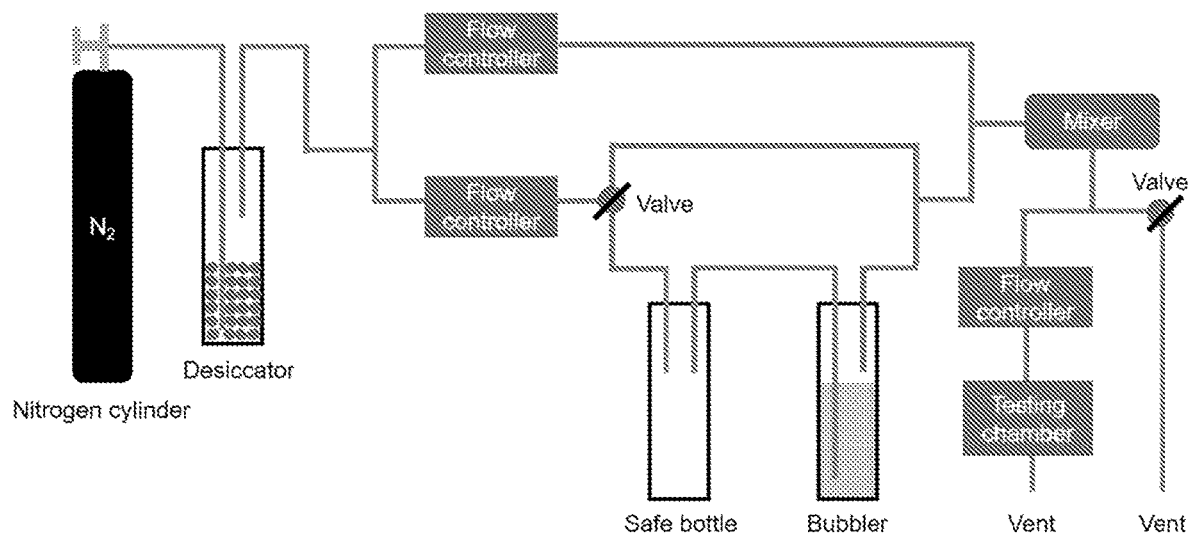
FIG. 24 shows the schematic of VOC vapor generation.

The electronic nose device was placed in a gas chamber with the dimension 5 cm×4 cm×2.5 cm (FIGS. 23A and 23B), and the real-time resistance change of each electrode was monitored continuously with the multimeter (Keithley Model 2000) and recorded by an in-house MATLAB software. VOC vapor was generated by bubbling VOC liquid with nitrogen carrier gas according to the literatures[59, 34, 60], as shown in FIG. 24. VOC vapors were prepared by diluting the saturated VOC vapor. The vapor pressures at the room temperature for ethanol, 2-ethylhexanol, nonanal and ethylbenzene were 5950 Pa, 30 Pa, 49 Pa and 1333 Pa, respectively. Therefore, the saturated concentration for ethanol, 2-ethylhexanol, nonanal and ethylbenzene were 58722 ppm, 296 ppm, 483 ppm and 13155 ppm, respectively. Two nitrogen streams firstly passed through the desiccant with the relative humidity of 8%. One nitrogen stream was used as the carrier gas and bubbled the VOC liquid to generate saturated VOC vapor. The other nitrogen stream was used as the diluting gas and mixed with saturated VOC vapor. Different concentrations of the VOC vapor was obtained by controlling the flow rates ratio of the carrier nitrogen and the diluting nitrogen. The flow rates of carrier gas and diluting gas for VOC vapors generation were summarized in Tables 9-12. The total flow rate into the gas chamber was controlled to be 1 L/min. The sensors arrays were exposed to VOC vapor for 2 min during responses measurements, followed by pure nitrogen exposure for 10 min for baseline recovery. In the stability test, the electronic nose was subjected to 10 cycles of VOC vapor exposure.

TABLE 9

Flow rates of carrier gas and diluting gas for ethanol vapor generation.

| Concentration (ppm) | 25 | 50 | 75 | 100 | 125 |
|---|---|---|---|---|---|
| Carrier gas (L/min) | 0.2 | 0.2 | 0.2 | 0.2 | 0.2 |
| Diluting gas (L/min) | 10.6 | 5.2 | 3.4 | 2.5 | 1.9 |

* The concentration of ethanol was firstly diluted to 1353 ppm before the vapor generation.

TABLE 10

Flow rates of carrier gas and diluting gas for 2-ethylhexanol vapor generation.

| Concentration (ppm) | 25 | 50 | 75 | 100 | 125 |
|---|---|---|---|---|---|
| Carrier gas (L/min) | 0.5 | 0.5 | 0.5 | 0.5 | 0.5 |
| Diluting gas (L/min) | 5.5 | 2.5 | 1.5 | 1.0 | 0.7 |

TABLE 11

Flow rates of carrier gas and diluting gas for nonanal vapor generation.

| Concentration (ppm) | 25 | 50 | 75 | 100 | 125 |
|---|---|---|---|---|---|
| Carrier gas (L/min) | 0.5 | 0.5 | 0.5 | 0.5 | 0.5 |
| Diluting gas (L/min) | 9.2 | 4.3 | 2.7 | 1.9 | 1.4 |

TABLE 12

Flow rates of carrier gas and diluting gas for ethylbenzene vapor generation.

| Concentration (ppm) | 25 | 50 | 75 | 100 | 125 |
|---|---|---|---|---|---|
| Carrier gas (L/min) | 0.5 | 0.5 | 0.5 | 0.5 | 0.5 |
| Diluting gas (L/min) | 8.1 | 3.8 | 2.4 | 1.6 | 1.2 |

* The concentration of ethanol was firstly diluted to 433 ppm before the vapor generation.

To obtain better cross-sensing ability, the electronic nose should include functionalized rGO with chemically diverse structures so that the functionalized rGO could have different interactions with the volatiles. In our experiment design, the selection of amine ligands was considered based on the chemical diversity and the availability. Amine ligands with various length of alkyl chain (ethylamine, hexylamine and octylamine) were chosen to endow the sensing materials with different polarity. Different aromaticity was also introduced by including benzylamine, 2-(4-chlorophenyl)ethylamine and tyramine. Besides, 1-(2-aminoethyl) piperidine and 1,3-diaminopropane offered other chemical diversity for the functionalization library development.

Statistics Processing and PCA

The resistance response was normalized as ΔR/R0. ΔR and R0 represent the resistance change under the exposure to VOCs and the baseline resistance under the nitrogen stream, respectively. PCA was calculated from the data matrix, in which nine columns were the peak responses from the nine sensing elements, and the rows represented each gas analyte measurements. Three repeating experiments for each VOC concentration were conducted. Real-time resistance response curves were analyzed with exponential curve fitting to study the response and recovery time of the sensing element.

REFERENCE

1. V. Dua, S. P. Surwade, S. Ammu, S. R. Agnihotra, S. Jain, K. E. Roberts, S. Park, R. S. Ruoff and S. K. Manohar, Angew. Chemie—Int. Ed., 2010, 49, 2154-2157.
2. Y. Dan, Y Lu, N. J. Kybert, Z. Luo and A. T C. Johnson, Nano Lett., 2009, 9, 1472-1475.
3. J. S. Kim, H. W. Yoo, H. O. Choi and H. T Jung, Nano Lett., 2014, 14, 5941-5947.
4. Z. Li and K. S. Suslick, ACS Sensors, 2016, 1, 1330-1335.
5. K. Persaud and G. Dodd, Nature, 1982, 299, 352.
6. M. S. Freund and N. S. Lewis, Proc. Natl. Acad. Sci., 1995, 92, 2652-2656.
7. W. Yang, P. Wan, M. Jia, J. Hu, Y Guan and L. Feng, Biosens. Bioelectron., 2015, 64, 547-553.
8. M. K. Nakhleh, H. Amal, R. Jeries, Y. Y. Broza, M. Aboud, A. Gharra, H. Ivgi, S. Khatib, S. Badameh, L. Har-Shai, L. Glass-Marmor, I. Lejbkowicz, A. Miller, S. Badamy, R. Winer, J. Finberg, S. Cohen-Kaminsky, F. Perros, D. Montani, B. Girerd, G. Garcia, G. Simonneau, F. Nakhoul, S. Baram, R. Salim, M. Hakim, M. Gruber, O. Ronen, T. Marshak, I. Doweck, O. Nativ, Z. Bahouth, D. Shi, W. Zhang, Q. Hua, Y. Pan, L. Tao, H. Liu. A. Karban, E. Koifman, T. Rainis, R. Skapars, A. Sivins, G. Ancans, I. Liepniece-Karele, 1. Kikuste, I. Lasina, 1. Tolmanis, D. Johnson, S. Z. Millstone, J. Fulton, J. W. Wells, L. H. Wilf, M. Humbert, M. Leja, N. Peled and H. Haick, ACS Nano, 2017, 11, 112-125.
9. J. T. Robinson, F. K. Perkins, E. S. Snow, Z. Wei and P. E. Sheehan. Nano Lett., 2008, 8, 3137-3140.
10. Miekisch. W. Schubert, J. K.; Noeldge-Schomburg, G. F. E. Clin. Chim. Acta 2004, 347, 25-39.
11. Cao. W.; Duan, Y. Clin. Chem. 2006, 52, 800-811.
12. Haick, H.; Broza, Y. Y.; Mochalski, P.; Ruzsanyi, V.; Amann, A. Chem. Soc. Rev. 2014, 43, 1423-1449.
13. Righettoni, M., Amann, A.; Pratsinis, S. E., Mater. Today 2015, 18, 163-171.
14. Boots, A. W.; Bos, L. D.; van der Schee, M. P.; van Schooten, F. J.; Sterk, P. J., Trends Mol. Med. 2015, 21, 633-644.
15. Hakim, M.; Broza, Y. Y.; Barash, O.; Peled, N. Phillips, M.; Amann, A.; Haick, H., Chem. Rev. 2012, 112, 5949-5966.
16. Rahman. I.; van Schadewijk, A. A. M.; Crowther, A. J. L.; Hiemstra, P. S.; Stolk, J.; MacNee, W. De Boer, W. I., Am. J. Respir. Crit. Care Med. 2002, 166, 490-495.
17. Marchitti, S. A.; Brocker, C.; Stagos, D.; Vasiliou, V., Drug Metab. Toxicol. 2008, 4, 697-720.
18. Deng, C.; Zhang, J.; Yu, X.; Zhang, W.; Zhang, X., J. Chromatogr. B 2004, 810, 269-275.
19. Van den Velde, S.; Nevens, F.; Van hee, P.; van Steenberghe, D.; Quirynen, M., J. Chromatogr. B 2008, 875, 344-348.
20. Persaud, K.; Dodd, G., Nature 1982, 299, 352-355.
21. Scott, S. M., James, D.; Ali, Z., Microchim. Acta 2006, 156, 183-207.
22. Röck, F.; Barsan, N.; Weimar, U., Chem. Rev. 2008, 108, 705-725.
23. Lu, Y. Yao, Y., Li, S., Zhang, Q., Liu, Q., 2017. Sens. Rev. 37, 396-403.
24. Huang, Z., Huang, C., Zhou, J., Li, J., Hui, G., 2017. Food Meas. 11, 33-40.
25. Shao, C., Zheng, H., Zhou, Z., Li, J., Lou. X., Hui, G., Zhao, Z., 2018. Food Anal. Methods 11, 3121-3129.
26. Ying, X., Liu, W., Hui, G., Ying, X., Liu, W., Hui, G., 2015. Bioengineered 6, 218-221.
27. Gilntner, A. T.; Pineau, N. J.; Mochalski, P.; Wiesenhofer, H.; Agapiou, A.; Mayhew, C. A.; Pratsinis, S. E., Anal. Chem. 2018, 90, 4940-4945.
28. Sysoev, V. V; Goschnick, J.; Schneider, T.; Strelcov, E.; Kolmakov, A., Nano Lett. 2007, 7, 3182-3188.
29. Freund, M. S.; Lewist, N. S., Proc. Natil. Acad. Sci. 1995, 92, 2652-2656.
30. Hatfield, J. V.; Neaves, P.; Hicks, P. J.; Persaud, K.; Travers, P., B. Chem. 1994, 18, 221-228.
31. Li, J.; Lu, Y.; Ye, Q.; Cinke, M.; Han, J.; Meyyappan, M., Nano Lett. 2003, 3, 929-933.
32. Star, A.; Joshi, V.; Skarupo, S.; Thomas, D.; Gabriel, J. C. P., J. Phys. Chem. B 2006, 110, 21014-21020.
33. Staii, C.; Johnson, A. T.; Chen, M.; Gelperin, A., Nano Lett. 2005, 5, 1774-1778.
34. Shirsat, M. D.; Sarkar, T. Kakoullis, J.; Myung, N. V; Konnanath, B.; Spanias, A.; Mulchandani, A., J. Phys. Chem. C 2012, 116, 3845-3850.
35. Peng, G.; Tisch, U.; Adams, O.; Hakim, M.; Shehada, N.; Broza, Y. Y.; Billan, S.; Abdah-Bortnyak, R.; Kuten, A.; Haick, H., Nat. Nanotechnol. 2009, 4, 669-673.
36. Nakhleh, M. K.; Amal, H.; Jeries, R.; Broza, Y. Y.; Aboud, M.; Gharra, A.; Ivgi, H.; Khatib, S.; Badameh, S.; Har-Shai, L.; et al., ACS Nano 2017, 11, 112-125.
37. Wongchoosuk, C.; Wisitsoraat, A.; Tuantranont, A.; Kerdcharoen, T., B Chem. 2010, 147, 392-399.
38. Zhu, X.; Liu, D.; Chen, Q.; Lin, L.; Jiang, S., Zhou, H.; Zhao, J.; Wu, J., Chem. Commun. 2016, 52, 3042-3045.
39. Kim, J. S.; Yoo, H. W.; Choi, H. O.; Jung, H. T., Nano Lett. 2014, 14, 5941-5947.
40. W. S. Hummers and R. E. Offeman, J. Am. Chem. Soc., 1958, 80, 1339.
41. Amal, H.; Ding, L.; Liu, B. Bin; Tisch, U.; Xu, Z. Q.; Shi, D. Y.; Zhao, Y; Chen, J.; Sun, R. X.; Liu, H.; et al., Int. J. Nanomedicine 2012, 7, 4135-4146.
42. Fuchs, P.; Loeseken, C.; Schubert, J. K.; Miekisch, W., Int. J. Cancer 2010, 126, 2663-2670.
43. Poli, D.; Carbognani, P.; Corradi, M.; Goldoni, M.; Acampa, O.; Balbi, B.; Bianchi, L.; Rusca, M.; Mutti, A., Respir. Res. 2005, 6, 1-10.
44. Yang, H.; Li, F.; Shan, C.; Han, D.; Zhang, Q.; Niu, L.; Ivaska, A., J. Mater. Chem. 2009, 19, 4632-4638.
45. Ren, Z.; Sun, D.; Zhang, J.; Yan, S., J. Mater. Chem. 2012, 22, 18839-18846.
46. Pu, X.; Zhang, H.-B.; Li, X.; Gui, C.; Yu, Z.-Z., RSC Adv. 2014, 4, 15297-15303.
47. Li, W.; Tang, X. Z.; Zhang, H. Bin; Jiang, Z. G.; Yu, Z. Z.; Du, X. S.; Mai, Y. W., Carbon 2011, 49, 4724-4730.
48. Lin, Z.; Liu, Y.; Wong, C. P., Langmuir 2010, 26, 16110-16114.
49. Kim, H. J.; Lee, J. H., B Chem. 2014, 192, 607-627.
50. Yuan, W.; Shi, G., J. Mater. Chem. A 2013, 1, 10078-10091.
51. Chiu, S., Tang, K., 2013. Sensors. 13, 14214-14247.
52. James, D., Scott, S. M., Ali, Z., O'Hare. W. T., 2005. Microchim. Acta 149, 1-17.
53. Kim, S. J., Choi, S. J., Jang, J. S., Kim, N. H., Hakim, M., Tuller, H. L., Kim, I. D., 2016, ACS Nano 10, 5891-5899.
54. Xie. C., Xiao, L., Hu, M., Bai. Z., Xia, X., Zeng, D., 2010. Sensors Actuators, B Chem. 145, 457-463.

55. Wang, B., Sonar, P. Manzhos, S., Haick. H., 2017. Sensors Actuators, B Chem. 251, 49-56.
56. Esteves, C. H. A., Iglesias, B. A., Li, R. W. C., Ogawa, T., Araki, K., Gruber, J., 2014. Sensors Actuators, B Chem. 193, 136-141.
57. Lipatov, A., Varezhnikov, A., Wilson, P., Sysoev, V., Kolmakov, A., Sinitskii, A., 2013. Nanoscale 5, 5426-5434.
58. Yuan, W.; Liu, A.; Huang, L.; Li, C.; Shi, G., Adv. Mater. 2013, 25, 766-771.
59. Dan, Y., Cao, Y; Mallouk, T. E.; Johnson, A. T.; Evoy, S., B Chem. 2007, 125, 55-59.
60. Zhu, X.; Zhang, H.; Wu, J., B Chem. 2014, 202, 105-113.
61. S. Basu and P. Bhattacharyya. Sensors Actuators B Chem., 2012, 173, 1-21.
62. Q. He, S. Wu, Z. Yin and H. Zhang, Chem. Sci., 2012, 3, 1764-1772.
63. H. Dai, Acc. Chem. Res., 2002, 35, 1035-1044.
64. Dickinson, T. A., White, J., Kauer J. S., Walt, D. R., 1996. Nature. 382, 697-700.
65. Haick, H., Broza, Y. Y., Mochalski, P., Ruzsanyi, V. Amann, A., 2014. Chem. Soc. Rev. 43, 1423-1449.
66. Miller. D. R., Akbar, S. A., Morris, P. A., 2014. Sensors Actuators B. Chem. 204, 250-272.
67. Rakow, N. A., Suslick, K. S., 20). Nature 406, 710-713.

The invention claimed is:

1. A method to synthesize amine functionalized reduced graphene oxide, comprising the steps of:
   a. Dispersing graphene oxide in an organic solvent to form a first solution;
   b. Reacting said first solution with one or more amines, an activation crosslinker and a catalyst;
   c. Obtaining a product from step (b) by centrifugation;
   d. Dispersing said product in DMF to form a second solution; and
   e. Reducing said product in said second solution to form said amine functionalized reduced graphene oxide.

2. The method of claim 1, wherein said organic solvent comprises toluene or benzene.

3. The method of claim 1, wherein said one or more amines are selected from the group consisting of ethylamine, hexylamine, octylamine, benzylamine, 2-(4-chloropenyl)ethylamine, 1-(2-aminoethyl)piperidine, 1,3-diaminopropane, amino poryphyrins and tyramine.

4. The method of claim 1, wherein said activation crosslinker comprises dicyclohexylcarbodiimide.

5. The method of claim 1, wherein said catalyst comprises 4-dimethyl-aminopyridine.

6. The method of claim 1, wherein said step (b) comprises heating said first solution to 80° C.

7. The method of claim 6, wherein said step (b) comprises stirring for 2 days.

8. The method of claim 1, wherein said product in said second solution is reduced using $NH_3$ and hydrazine.

9. The method of claim 1, wherein said step (e) comprises heating said second solution to 90° C.

10. A sensor array for detecting at least one target chemical in a sample, comprising:
    a plurality of sensing elements, each sensing element comprising an amine functionalized reduced graphene oxide synthesized by the method of claim 1 using a different amine;
    wherein each sensing element exhibits a different resistance response when exposed to said target chemical to produce a response pattern specific to said target chemical.

11. The sensor array of claim 10, wherein said amine comprises an organic amine.

12. The sensor array of claim 11, wherein said organic amine is selected from the group consisting of ethylamine, hexylamine, octylamine, benzylamine, 2-(4-chlorophenyl)ethylamine, 1-(2-aminoethyl)piperidine, 1,3-diaminopropane, amino poryphyrins and tyramine.

13. The sensor array of claim 10, wherein said sensor array further comprises a sensing element comprising non-modified reduced graphene oxide.

14. The sensor array of claim 10, wherein said at least one target chemical is selected from the group consisting of toluene, ethyl acetate, ethanol, acetone, hexane, 2-ethylhexanol, nonanal, 3-methylhexane, 5-ethyl-3-methyloctane, iso-nonane, isoprene, styrene, undecane and ethylbenzene.

15. The sensor array of claim 10, wherein said sensing elements have a sensitivity of at least 25 ppm.

16. The sensor array of claim 10, wherein said sensor array functions at room temperature.

* * * * *